US012139706B2

(12) United States Patent
Becker et al.

(10) Patent No.: US 12,139,706 B2
(45) Date of Patent: *Nov. 12, 2024

(54) METHOD OF NONSPECIFIC TARGET CAPTURE OF NUCLEIC ACIDS

(71) Applicant: Gen-Probe Incorporated, San Diego, CA (US)

(72) Inventors: Michael M. Becker, San Diego, CA (US); Mehrdad R. Majlessi, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 472 days.

This patent is subject to a terminal disclaimer.

(21) Appl. No.: 17/126,693

(22) Filed: Dec. 18, 2020

(65) Prior Publication Data

US 2021/0102201 A1    Apr. 8, 2021

Related U.S. Application Data

(60) Continuation of application No. 14/990,508, filed on Jan. 7, 2016, now Pat. No. 10,900,033, which is a division of application No. 13/769,226, filed on Feb. 15, 2013, now abandoned, which is a continuation of application No. 11/832,367, filed on Aug. 1, 2007, now Pat. No. 9,051,601.

(60) Provisional application No. 60/821,078, filed on Aug. 1, 2006.

(51) Int. Cl.
| | |
|---|---|
| *C12N 15/11* | (2006.01) |
| *C07H 21/02* | (2006.01) |
| *C07H 21/04* | (2006.01) |
| *C12N 15/10* | (2006.01) |
| *C12Q 1/6806* | (2018.01) |
| *C12Q 1/6834* | (2018.01) |
| *C12Q 1/70* | (2006.01) |

(52) U.S. Cl.
CPC ............ *C12N 15/11* (2013.01); *C07H 21/02* (2013.01); *C07H 21/04* (2013.01); *C12N 15/1006* (2013.01); *C12Q 1/6806* (2013.01); *C12Q 1/6834* (2013.01); *C12Q 1/70* (2013.01); *C12N 2310/18* (2013.01); *C12N 2310/31* (2013.01); *C12N 2310/321* (2013.01); *C12N 2310/351* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 5,039,606 A * | 8/1991 | Nepon | C12Q 1/6883 435/6.12 |
| 5,043,272 A | 8/1991 | Hartley | |
| 5,283,174 A | 2/1994 | Arnold, Jr. et al. | |
| 5,312,728 A | 5/1994 | Lizardi et al. | |
| 5,427,930 A | 6/1995 | Birkenmeyer et al. | |
| 5,475,096 A | 12/1995 | Gold et al. | |
| 5,512,439 A | 4/1996 | Hornes et al. | |
| 5,512,463 A | 4/1996 | Stemmer | |
| 5,599,667 A | 2/1997 | Arnold, Jr. et al. | |
| 5,834,198 A | 11/1998 | Famulok et al. | |
| 5,994,058 A | 11/1999 | Senapathy | |
| 6,060,246 A | 5/2000 | Summerton et al. | |
| 6,110,678 A | 8/2000 | Weisburg et al. | |
| 6,130,038 A | 10/2000 | Becker et al. | |
| 6,268,147 B1 | 7/2001 | Beattie et al. | |
| 6,280,952 B1 | 8/2001 | Weisberg et al. | |
| 6,326,479 B1 | 12/2001 | Gildea et al. | |
| 6,383,752 B1 | 5/2002 | Agrawal et al. | |
| 6,455,248 B1 | 9/2002 | Bhattacharjee et al. | |
| RE37,891 E | 10/2002 | Collins et al. | |
| 6,534,273 B2 | 3/2003 | Weisberg et al. | |
| 6,835,542 B2 | 12/2004 | Becker et al. | |
| 6,849,412 B2 | 2/2005 | Becker et al. | |
| 6,936,467 B2 | 8/2005 | Kmiec et al. | |
| 7,005,261 B1 | 2/2006 | Lloyd et al. | |
| 7,022,835 B1 | 4/2006 | Rauth et al. | |
| 7,052,844 B2 | 5/2006 | Atkinson et al. | |
| 7,153,433 B2 | 12/2006 | Kolzau et al. | |
| 7,169,894 B2 | 1/2007 | Martin | |

(Continued)

FOREIGN PATENT DOCUMENTS

| | | |
|---|---|---|
| EP | 0 328 829 A2 | 8/1989 |
| WO | 199850583 A1 | 11/1998 |

(Continued)

OTHER PUBLICATIONS

PCT, International Search Report and Written Opinion, International Application No. PCT/US2007/074990, mailed Nov. 14, 2007.
PCT International Preliminary Report on Patentability, International Application No. PCT/US2007/074990, Aug. 1, 2007 (Jan. 8, 2007) (Date of Issuance of Report—Feb. 3, 2009 (Mar. 2, 2009)).
International Preliminary Report on Patentability, International Application No. PCT/US2007/074990, issued Feb. 3, 2009.
Extended European Search Report in corresponding European application 07813662.9 dated May 7, 2010 (6 pp).

(Continued)

*Primary Examiner* — Samuel C Woolwine
(74) *Attorney, Agent, or Firm* — Jeffrey E. Landes; Alston & Bird LLP

(57) ABSTRACT

Methods for capturing a target nucleic acid from a sample by using a capture probe that binds nonspecifically to the target nucleic acid and binds specifically to an immobilized probe via a specific binding pair that has one member on the capture probe and one member on the immobilized probe are disclosed. Compositions that include a capture probe that binds nonspecifically to a target nucleic acid and specifically to an immobilized probe via binding of members of a specific binding pair in a solution phase of a reaction mixture are disclosed.

20 Claims, No Drawings

Specification includes a Sequence Listing.

(56) References Cited

U.S. PATENT DOCUMENTS

| | | | |
|---|---|---|---|
| 7,235,386 | B2 | 6/2007 | Padgett et al. |
| 7,255,992 | B2 | 8/2007 | Ecker et al. |
| 7,348,185 | B2 | 3/2008 | Yamamichi |
| 9,051,601 | B2 | 6/2015 | Becker et al. |
| 2001/0053519 | A1 | 12/2001 | Fodor et al. |
| 2002/0028459 | A1 | 3/2002 | Weisburg et al. |
| 2002/0110810 | A1* | 8/2002 | Shuber .................. C12Q 1/689 435/6.15 |
| 2002/0197614 | A1 | 12/2002 | Weir et al. |
| 2004/0023207 | A1 | 2/2004 | Polansky |
| 2004/0043468 | A1 | 3/2004 | Mauro et al. |
| 2004/0209298 | A1 | 10/2004 | Kamberov et al. |
| 2004/0235138 | A1* | 11/2004 | Weisburg ............. C12Q 1/6893 435/252.3 |
| 2005/0037988 | A1 | 2/2005 | Zamore et al. |
| 2005/0164220 | A1 | 7/2005 | Gretardsdottir et al. |
| 2005/0164223 | A1* | 7/2005 | Schalken ............. C12Q 1/6886 435/6.14 |
| 2005/0221490 | A1 | 10/2005 | Tuschl et al. |
| 2006/0128650 | A1 | 6/2006 | Xu |
| 2006/0134787 | A1 | 6/2006 | Zamore et al. |
| 2007/0161015 | A1* | 7/2007 | Zheng .................. C12Q 1/6837 435/6.15 |
| 2013/0209992 | A1 | 8/2013 | Becker et al. |

FOREIGN PATENT DOCUMENTS

| | | | |
|---|---|---|---|
| WO | 0026412 | A1 | 5/2000 |
| WO | 2008016988 | A1 | 2/2008 |

OTHER PUBLICATIONS

EP Communication Pursuant to Article 94(3) in corresponding EP Patent Application 07813662.9 dated Mar. 15, 2011.
Communication pursuant to Article 94(3) EPC, European Patent Application No. 07813662.9, dated Jan. 5, 2012.
Communication pursuant to Article 94(3) EPC, European Patent Application No. 07813662.9, dated Apr. 26, 2013.
EPO, Extended European Search Report, European Application No. 16195957.2, dated Jan. 19, 2017.
Non-final Office Action, U.S. Appl. No. 11/832,367, issued Feb. 18, 2010.
Final Rejection, U.S. Appl. No. 11/832,367, issued Sep. 9, 2010.
USPTO, Advisory Action, U.S. Appl. No. 11/832,367, dated Nov. 16, 2010.
USPTO, Advisory Action, U.S. Appl. No. 11/832,367, dated Jan. 14, 2011.
Non-final Rejection, U.S. Appl. No. 11/832,367, issued Mar. 10, 2014.
Final Rejection, U.S. Appl. No. 11/832,367, issued Jun. 16, 2014.
USPTO, Notice of Allowance and Examiner Interview Summary, U.S. Appl. No. 11/832,367, dated Feb. 13, 2015.
USPTO, Corrected Notice of Allowance and Examiner Interview Summary, U.S. Appl. No. 11/832,367, dated Apr. 3, 2015.
USPTO, Non-Final Rejection, U.S. Appl. No. 13/769,226, dated Jan. 16, 2015.
USPTO, Final Rejection, U.S. Appl. No. 13/769,226, dated Oct. 7, 2015.
Examiner's First Report, Australian Patent Application No. 2011203508, dated Feb. 22, 2012.
APO, Notice of Acceptance, Australian Application No. 2011203508, dated Apr. 4, 2012.
Japanese Office Action dated Jan. 7, 2013, Japanese Patent Application No. 2009-523046.
Notice of Reasons for Rejection, Japanese Patent Application No. 2009-523046, mailed Nov. 26, 2013.
Notice of Reasons for Rejection, Japanese Patent Application No. 2009-523046, mailed Jul. 9, 2014.
JPO, Notice of Allowance, Japanese Application No. 2009-523046, dated Oct. 10, 2014.
JPO, Office Action, Japanese Application No. 2013-048876, dated Jul. 9, 2014.
JPO, Office Action, Japanese Application No. 2013-048876, dated Apr. 6, 2015.
JPO, Notice of Final Rejection, Japanese Application No. 2015-198504, dated Sep. 06, 2016.
JPO, Notice of Final Rejection, Japanese Application No. 2015-198504, dated Aug. 30, 2017.
EPO, Extended European Search Report, European Application No. 13160839.0, dated Jul. 16, 2014.
EPO, Communication pursuant to Article 94(3) EPC, European Application No. 13160839.0, dated Aug. 5, 2015.
EPO, Communication pursuant to Article 94(3) EPC, European Application No. 13160839.0, dated Jan. 4, 2016.
EPO, Communication under Rule 71(3) EPC, European Application No. 13160839.0, dated Jul. 8, 2016.
Requisition by the Examiner, Canadian Patent Application No. 2,658,105, dated Oct. 23, 2013.
CIPO, Examination Report, Canadian Application No. 2,658,105, dated Dec. 2, 2014.
Gene Link Random Cy3 labeled primers [online] Jan. 14, 2003 [retrieved on Apr. 28, 2013] retrieved from http://web.archive.org/web/20030114183830/http://www.genelink.com/geneprodsite/category.asp?c=71 (Year: 2003).
Gene Link Random Primers description [online] Aug. 28, 2005 [retrieved on Apr. 28, 2013] retrieved from http://web.archive.org/web/20050828014046/http://www.genelink.com/geneprodsite/category.asp?c=81 (Year: 2005).
Gene Link Random Cy3 labeled primers [online] Jul. 21, 2006 [retrieved on Apr. 28, 2013] retrieved from http://web.archive.org/web/20060721040907/http://www.genelink.com/geneprodsite/category.asp?c= 71 (Year: 2006).
Gen Bank L22579 [online] Jan. 12, 1995 [retrieved on Aug. 20, 2018, retrieved from: https://www.ncbi.nlm.gov/nuccore/L22579.1 (Year: 1995).
"Oligonucleotide Synthesis" [online] [retrieved on Feb. 13, 2018] retrieved from https://en.wikipedia.org/wiki/Oligonucleotide_synthesis (17 pages). (Year: 2018).
Santa Cruz Biotechnology anti-Cy3 datasheet [online] [retrieved on Jan. 2, 2020] retrieved from https://datasheets.scbt.com/sc-166894.pdf (Year: 2020).
Baeumner, et al., "A Universal Nucleic Acid Sequence Biosensor with Nanomolar Detection Limits", Analytical Chemistry, vol. 76, No. 4, 888-894, Feb. 15, 2004.
Fritz, et al., "A novel 3' extension technique using random primers in RNA-PCR", Nucleic Acids Research, Jul. 11, 1991, vol. 19, No. 13, p. 3747, Oxford University Press.
Protozanova et al. Formation of DNA Frayed Wires is Independent of the Directionality of the Parent Strand. Biopolymers 58:355-358. (Year: 2001).
Yanagisawa et al. Diversity and similarity among recognition sequences of Dof transcription factors. the Plant Journal 17(2):209-214. (Year: 1999).

\* cited by examiner

METHOD OF NONSPECIFIC TARGET CAPTURE OF NUCLEIC ACIDS

RELATED APPLICATIONS

This application is a continuation of U.S. application Ser. No. 14/990,508, filed Jan. 7, 2016, allowed, which is a divisional of U.S. application Ser. No. 13/769,226, is a continuation of U.S. application Ser. No. 11/832,367, filed Aug. 1, 2007, which claims the benefit under 35 U.S.C. 119(e) of U.S. Provisional Application Ser. No. 60/821,078, filed Aug. 17, 2006, each of which is hereby incorporated by reference.

REFERENCE TO SEQUENCE LISTING SUBMITTED AS A TEXT FILE VIA EFS WEB

The Sequence Listing written in file GP196-04-DV1_ST25.txt is 17 kilobytes in size, was created Jan. 7, 2016, and is incorporated by reference.

FIELD

The disclosed compositions and methods relate to molecular biology, more particularly to methods and compositions for nucleic acid isolation from a mixture, such as a sample, by using a nucleic acid oligomer that hybridizes nonspecifically to a target nucleic acid to separate it from other components of the mixture.

BACKGROUND

Many molecular biology procedures such as in vitro amplification and in vitro hybridization of nucleic acids include some preparation of nucleic acids to make them effective in the subsequent procedure. Methods of nucleic acid purification may isolate all nucleic acids present in a sample, isolate different types of nucleic acids based on physical characteristics, or isolate specific nucleic acids from a sample. Many methods involve complicated procedures, use harsh chemicals or conditions, or require a long time to complete the nucleic acid isolation. Some methods involve use of specialized oligonucleotides, each specific for an intended target nucleic acid which adds complexity to the design, optimization and performance of methods, particularly if isolation of more than one target nucleic acid is desired or if the sequence of the desired target nucleic acid is unknown. Thus, there remains a need for a simple, efficient, and fast method to separate nucleic acids of interest from other sample components.

SUMMARY

A method is disclosed for isolating a target nucleic acid from a sample that includes: (a) mixing a sample containing a target nucleic acid with a nonspecific capture probe made up of an oligonucleotide sequence that hybridizes nonspecifically with the target nucleic acid and a means for linking the target nucleic acid to a support, in which the oligonucleotide sequence is a poly-U sequence, a random poly-(k) sequence comprising G and T nucleotides or G and U nucleotides, two random oligonucleotide sequences separated by a non-random sequence consisting of 10 or fewer nucleotides, two random oligonucleotide sequences separated by a non-random sequence consisting of 10 or fewer nucleotide base analogs, two random oligonucleotide sequences separated by a non-nucleotide spacer compound, a plurality of random oligonucleotide sequences separated by non-random sequences consisting of 10 or fewer nucleotides or nucleotide base analogs, a plurality of random oligonucleotide sequences separated by non-nucleotide spacer compounds, or a non-random poly-GU sequence made up of at least two GU units. The method steps also include incubating a reaction mixture containing the support, the target nucleic acid, and the nonspecific capture probe in hybridization conditions that allow nonspecific hybridization of the capture probe and the target nucleic acid to form a hybridization complex linked to the support, and separating the support from a solution phase of the reaction mixture to separate the hybridization complex linked to the support from other sample components, thereby isolating the target nucleic acid from other sample components. In one embodiment, the means for linking the target nucleic acid to the support is direct attachment of the capture probe to the support. In another embodiment, the means for linking the target nucleic acid to the support is a specific binding pair made up of a first specific binding partner (SBP) attached to the capture probe that binds specifically to a second specific binding partner (SBP') that is linked to the support. In one embodiment, the SBP' is part of an immobilized probe that is linked to the support. In the method, the mixing step includes mixing the sample with the SBP attached to the capture probe and the SBP' linked to the support, and the incubating step includes binding the SBP and the SBP' to link the hybridization complex to the support. In some embodiments, the SBP and the SBP' are substantially complementary nucleic acid sequences, whereas in other embodiments, the SBP and the SBP' are non-nucleic acid moieties. The non-nucleic acid moieties may be selected from the group consisting of (a) a receptor and ligand pair, (b) an enzyme and substrate pair, (c) an enzyme and cofactor pair, (d) an enzyme and coenzyme pair, (e) an antibody and antigen pair, (f) an antibody fragment and antigen pair, (g) a sugar and lectin pair, (h) a ligand and chelating agent pair, (i) biotin and avidin, (j) biotin and streptavidin, and (k) nickel and histidine. The method may also include a washing step after the separating step to remove other sample components from the hybridization complex linked to the support, in which the washing step mixes the hybridization complex linked to the support with a washing solution and then separates the hybridization complex linked to the support from the washing solution. The incubating step may be performed at about 25° C. for about 5 minutes to about 90 minutes. The method may also include a step after the separating step of detecting the presence of the target nucleic acid isolated from other sample components, amplifying in vitro a sequence contained in the target nucleic acid isolated from other sample components, or determining a sequence contained the target nucleic acid isolated from other sample components.

A nonspecific capture probe is disclosed that is made up of a first specific binding partner (SBP) that binds specifically to a second specific binding partner (SBP') linked to a support and an oligonucleotide sequence that hybridizes nonspecifically to a target nucleic acid, in which the oligonucleotide sequence is a poly-U sequence, a random poly-(k) sequence comprising G and T nucleotides or G and U nucleotides, two random oligonucleotide sequences separated by a non-random sequence consisting of 10 or fewer nucleotides, two random oligonucleotide sequences separated by a non-random sequence consisting of 10 or fewer nucleotide base analogs, a plurality of random oligonucleotide sequences separated by non-random sequences consisting of 10 or fewer nucleotides or nucleotide base analogs, two random oligonucleotide sequences separated by a non-nucleotide spacer compound, a plurality of random oligonucleotide sequences separated by non-nucleotide spacer compounds, or a non-random poly-GU sequence made up of at least two GU units. The capture probe's oligonucleotide sequence may be of about 5 to 100 nucleotides in length, and in some embodiments is about 12 to about 25 nucleotides in length. The oligonucleotide sequence may contain: (a) standard RNA bases and linkages, (b) standard DNA bases and linkages, (c) RNA bases with 2' modified linkages, (d) DNA bases in which at least part of the sequence is in a locked nucleic acid (LNA) conformation, (e) one or more nucleotide base analogs, (f) one or more abasic residues, (g) one or more non-nucleic acid spacer compounds, or (h) a combination of elements selected from groups (a) to (g) above. In some embodiments, the oligonucleotide sequence contains base analogs that exhibit alternative base pairing properties compared to standard DNA or RNA base pairing. In some embodiments, those base analogs are inosine or 5-nitroindole. The oligonucleotide sequence may contain a mixture of nucleotides in LNA conformation and standard DNA conformation. In some embodiments, the oligonucleotide is made of poly(k) RNA bases with 2' modified linkages. The capture probe's SBP that binds specifically to the SBP' is a member of a specific binding pair that may be: (a) a pair of complementary nucleic acid sequences, (b) a receptor and ligand pair, (c) an enzyme and substrate pair, (d) an enzyme and cofactor pair, (e) an enzyme and coenzyme pair, (f) an antibody and antigen pair, (g) an antibody fragment and antigen pair, (h) a sugar and lectin pair, (i) a ligand and chelating agent pair, (j) biotin and avidin, (k) biotin and streptavidin, and (l) nickel and histidine. The oligonucleotide sequence may be linked to the SBP at a 5' terminal position of the oligonucleotide, a 3' terminal position of the oligonucleotide, or at an internal position of the oligonucleotide via a linker compound. In some embodiments, the oligonucleotide sequence comprises at least one random poly-$(k)_6$ sequence, and other embodiments include those that include a random poly-$(k)_{12}$, poly-$(k)_{18}$, or poly-$(k)_25$ sequence. Preferred capture probe embodiments include those in which the oligonucleotide sequence is a $(n)_6$-$U_3$-$(n)_6$ sequence, a $(n)_6$-$Ni_5$-$(n)_6$ sequence in which "Ni" stands for 5-nitroindole, a $(k)_6$-$Ni_5$-$(k)_6$ sequence in which "Ni" stands for 5-nitroindole, a $(k)_6$-C9-C9-$(k)_6$ sequence in which "C9" stands for a 9 carbon non-nucleotide spacer, a $(k)_6$-C9-$(k)_6$-C9-$(k)_6$ sequence in which "C9" stands for a 9 carbon non-nucleotide spacer, a $(k)_{12}$ sequence, a $(k)_6$-$U_3$-$(k)_6$ sequence, a $(k)_6$-$U_6$-$(k)_6$ sequence, a $(k)_6$-$T_3$-$(k)_6$ sequence, a $(k)_{18}$ sequence, a $(k)_24$ sequence, a d(G or Mg sequence, a $U_{18}$ sequence, a $(GU)_9$ sequence, or sequences in which "L" denotes a locked nucleic acid conformation, which include a L$(k)_6$-$dT_3$-L$(k)_6$ sequence), a L$(k)_4$-$d(k)_2$-$dT_3$-L$(k)_4$-$d(k)_2$ sequence, a L$(k)_4$-$d(k)_3$-L$(k)_4$-$d(k)_3$-L$(k)_4$ sequence, a L$(k)_3$-$d(k)_3$-L$(k)_3$-$d(k)_3$-L$(k)_3$-$d(k)_3$ sequence, a L(k)6-dT3-L(k)6 sequence, a L$(k)_4$-$d(k)_2$-$dT_3$-L$(k)_4$-$d(k)_2$ sequence, a L$(k)_2$-$d(k)_4$-L$(k)_2$-$d(k)_4$-L$(k)_2$-$d(k)_4$ sequence, a d$(k)_6$-$dT_3$-L$(k)_6$ sequence, and a L$(k)_4$-$d(k)_3$-L$(k)_4$-$d(k)_3$-L$(k)_4$-$d(k)_3$-L$(k)_4$ sequence. In other preferred embodiments, any of the above specified oligonucleotide sequences may be joined to a homopolymeric nucleic acid sequence that is the SBP of the capture probe.

DETAILED DESCRIPTION

A method is disclosed for isolating a target nucleic acid of interest from a sample that includes the steps of mixing a sample containing a target nucleic acid with a capture probe that hybridizes nonspecifically to a target nucleic acid in a sample in a solution phase, in which the capture probe contains a polymer oligonucleotide sequence that hybridizes nonspecifically to a target nucleic acid, preferably by using a polymer sequence that contains a poly-G/U or a poly-(k) sequence. The capture probe also includes a means for attaching it to a support, preferably via a specific binding partner that binds specifically to an immobilized probe attached to the support. A reaction mixture is made containing the target nucleic acid and the capture probe in a solution phase, and the support which optionally may include the immobilized probe. The reaction mixture is incubated under conditions in which the capture probe hybridizes nonspecifically to the target nucleic acid, and, if the immobilized probe is present, binds specifically to the immobilized probe via binding of the specific binding partners of the capture probe and the immobilized probe. The hybridization complex that includes the target nucleic acid and the capture probe attached to the support is separated from the reaction mixture to isolate the target nucleic acid from other sample components.

A probe for nonspecific capture of a target nucleic acid is disclosed that includes at least one nucleic acid sequence that hybridizes nonspecifically to the target nucleic acid and a means for attaching the capture probe to a support, preferably by including at least one specific binding partner that binds specifically to another specific binding partner on an immobilized probe attached to the support. That is, the specific binding partner of the capture probe and the specific binding partner of the immobilized probe are members of a specific binding pair. Preferred embodiments of capture probes include those in which the nucleic acid sequence that hybridizes nonspecifically to the target nucleic acid includes at least one poly-GU sequence, or a random poly-(k) sequence, or a sequence that includes at least one nucleic acid analog that exhibits alternative base pairing properties for the target nucleic acid compared to standard base pairing of nucleic acids.

The disclosed methods of target capture isolate a target nucleic acid from a sample by using nonspecific hybridization of a sequence in a capture probe to the target nucleic acid, where the capture probe includes at least one sequence that exhibits alternative base pairing properties for the target nucleic acid compared to standard base pairing (i.e., G:C and A:T/U bonding). The target nucleic acid may be RNA or DNA, which may be in single-stranded, or completely or partially double-stranded forms. Preferred capture probe polymer sequences with alternative base pairing properties include those that contain one or more nonrandom or random poly-(k) segments or portions, in which "k" is guanine (G) and thymine (T) or uracil (U) bases in an oligonucleotide, those that include one or more base analogs or derivatives, and those that contain alternative conformations compared to standard RNA or DNA. A sequence in a probe that exhibits alternative base pairing properties may include one or more of these characteristics in a single oligomer, e.g., poly-(k) segments with one or more residues in alternative conformations, as illustrated by some of the preferred embodiments described herein. A capture probe that exhibits alternative base pairing properties may be joined directly or indirectly to a support. Preferred capture probe embodiments include a specific binding partner (SBP) that binds specifically with another specific binding partner (SBP') present in an immobilized probe to link the capture probe to a support. The SBP and SBP' are members of a specific binding pair, which may be any of a variety of moieties that bind specifically. A capture probe that includes at least one sequence with alternative base pairing properties linked to a specific binding partner (SBP) may link the two components at any position of the capture probe compound, e.g., as represented by the structures "nonspecific polymer-SBP" or "SBP-nonspecific polymer" or "SBP-poly-(k)"or "poly-(k)-SBP". The SBP of the capture probe may be linked at either terminal position of the polymer sequence or linked to an internal position of the capture probe polymer. Some embodiments of capture probes include multiple random polymer sequences linked by short nucleotide sequences, e.g., a homopolymer sequence, or linked by non-nucleotide spacer compounds, e.g., a nine carbon spacer compound (C-9). Some embodiments of capture probes include standard DNA or RNA linkages, although a variety of nonstandard linkages may be included in a capture probe. Some preferred embodiments include in the capture probe one or more bases in a locked nucleic acid (LNA) conformation, which may provide a functional bias to the capture probe for binding to a preferred target nucleic acid form, such as preferentially binding to DNA. In some embodiments, the SBP of a capture probe is an oligonucleotide sequence that hybridizes specifically to a complementary sequence (SBP') of the immobilized probe, i.e., the specific binding pair is made up of substantially complementary oligonucleotide sequences. In other embodiments, the SBP of the capture probe is a moiety that binds specifically to a ligand moiety, i.e., the two moieties make up a specific binding pair. Examples of specific binding pairs are well known, such as a binding pair made up of an antibody or antibody fragment and it's antigen or ligand, or made up of an enzyme and its substrate or cofactor, or made up of a receptor and its binding partner or an analog thereof, which may generally referred to as any pair of compounds that function in a lock-and-key manner.

In the disclosed methods, the capture probe hybridizes nonspecifically to one or more target nucleic acids present in a mixture, such as a sample to be tested, and then the hybridization complex that includes the target nucleic acid and the capture probe attached directly or indirectly to a support is separated from the other components in the mixture. In preferred embodiments, the capture probe's random polymer sequence hybridizes nonspecifically to one or more sequences present in the target nucleic acid(s) and the capture probe's SBP binds specifically to the SBP' of the immobilized probe which is attached to the support so that the support with the attached complex that includes the capture probe and the target nucleic acid is separated from other components in the mixture. In some preferred embodiments, the complex attached to the support is washed to further remove other sample components from the captured target nucleic acid. The target nucleic acid may be subjected to subsequent additional steps to identify, quantify, or otherwise use the isolated target nucleic acid. Such additional steps may include a detection step, a hybridization step, a nucleic acid amplification step, a sequencing step, and the like. Preferred embodiments use a minimum of steps to make a target capture reaction mixture that includes the target nucleic acid, the capture probe and a support, optionally with an immobilized probe. The reaction mixture is incubated at relatively mild conditions to allow nonspecific hybridization of the capture probe to the target nucleic acid, e.g., room temperature to 60° C., for less than two hours.

It will be appreciated that the methods described herein may be used in parallel or in a sequential manner to preferentially capture different target nucleic acids from one or more samples. For example, one sample may be divided into different portions, each portion subjected to target capture steps by using a different embodiment of a capture probe that preferentially captures a different type of target nucleic acid. For example, one portion may be subjected to target capture by using a capture probe that preferentially separates DNA from the other sample components, whereas another portion may be subjected to target capture by using a capture probe that preferentially separates RNA from the other sample components, thereby preferentially separating the DNA from RNA components of the same sample. Alternatively, a sample may be treated in a sequential manner by using different capture probes that preferentially separate different target nucleic acids. For example, a sample may be subjected to a first target capture by using a capture probe that preferentially separates DNA from the other sample components, so that DNA targets are first separated (pellet portion) from the solution phase, and then the solution phase (supernatant portion) is subjected to a second target capture by using a capture probe that preferentially separates RNA from other sample components, thereby separating the DNA and RNA targets contained in the same sample in a series of target capture reactions.

A preferred embodiment of a capture probe includes at least one random polymer sequence that hybridizes nonspecifically with a target nucleic acid and a specific binding partner (SBP). In some embodiments, the random polymer sequence is a poly-(k) sequence, in which "k" is a random assortment of guanine (G) and uracil (U) or thymine (T) bases in an oligonucleotide. The random polymer sequence is typically in a range of about five to about 100 nucleotides in length, preferably in a range of about 6 to about 25 nucleotides. The SBP binds specifically with another specific binding partner (SBP') joined to a support, preferably in an immobilized probe. The SBP and SBP' members of a specific binding pair, which may be any moieties that bind specifically, e.g., complementary nucleic acid sequences, antibody-antigen pairs, receptor-ligand pairs, enzyme-substrate or enzyme-cofactor pairs, biotin and avidin or streptavidin, and the like. The capture probe's random sequence may be linked to the SBP at any position of the compound, e.g., at a 5' or 3' terminal position of an oligonucleotide, or at an internal position via a linker compound. A capture probe containing such components may be represented as SBP-random polymer, or random polymer-SBP, or, in preferred embodiments, SBP-poly-(k) or poly-(k)-SBP structures. Some embodiments of capture probes include multiple random sequences linked in a contiguous compound, such as random segments linked by non-random sequences or non-nucleotide spacer compounds. For example, preferred embodiments may include one or more homopolymeric sequences (e.g., $dT_3$) or non-nucleotide spacers (e.g., C-9 compound) separating segments of random sequences. Some capture probe embodiments include standard DNA or RNA linkages, whereas others may include synthetic linkages that provide functional properties to the capture polymer, such as preferential binding to a particular type of target nucleic acid. For example, some embodiments of capture probe oligonucleotides include one or more residues in locked nucleic acid (LNA) conformation or protein/peptide nucleic acid (PNA) conformation, or one or more 2'-methoxy or 2'-fluoro substituted RNA residues, or other nucleic acid analogue conformations. Preferred embodiments include one or more residues in LNA conformation for capture probes that preferentially bind to DNA targets, or include one or more 2'-methoxy substituted RNA residues for capture probes that preferentially bind to RNA targets. In preferred embodiments, the SBP and the SBP' are substantially complementary oligonucleotide sequences, i.e., the capture probe includes a SBP sequence that hybridizes specifically to the SBP' sequence of an immobilized probe. In other preferred embodiments, the SBP is a non-nucleic acid moiety that binds specifically to a SBP' ligand moiety of the immobilized probe.

In some embodiments, the capture probe is a composition used in target capture, preferably as part of a reagent mixture used in a target capture reaction. Such a reagent may include other components, such as an immobilized probe, a SBP' moiety joined to a support, and/or chemical compounds which in solution phase provide conditions for nucleic acid hybridization (e.g., salts, buffering agents). A capture probe reagent may be included in a composition, such as a kit, that includes other components used in target capture steps, e.g. a wash solution to remove sample components from the captured target nucleic acid. A capture probe reagent may be included in a composition, such as a kit, that includes other components used in subsequent steps to treat the captured nucleic acid, e.g., a dye to bind to and detect the captured nucleic acid, a detection probe to hybridize to and detect the captured nucleic acid, or an amplification oligonucleotide that binds the target nucleic acid and serves as a primer for in vitro amplification of a target sequence. Preferred kit embodiments contain a solution that contains a capture probe oligomer as described herein with an immobilized probe that provides the SBP' for the capture probe's SBP. It will be appreciated that a kit may include more than one capture probe embodiment, e.g., a first capture probe that includes a first SBP, and a second capture probe that includes a second SBP. Such compositions may be useful for preferentially capturing different target nucleic acids from one or more samples by using different immobilized probes, e.g., a first immobilized probe with a first SBP' specific for the first SBP, and a second immobilized probe with a second SBP' specific for the second SBP.

Methods and compositions described herein are useful for purifying nucleic acid sequences from a complex mixture, such as from a sample that contains nucleic acids or cells, which may be treated by using conventional methods to release intracellular nucleic acids into a solution. These compositions and methods are useful for preparing nucleic acids for use in many molecular biology procedures, e.g., in vitro amplification and/or detection steps used in diagnostic assays, forensic tests to detect the presence of biological material, or assays to detect biological contaminants in environmental, industrial, or food samples. The target capture methods and compositions concentrate target nucleic acids from a sample in which they may be a minor component to improve sensitivity of detection. The target capture compositions and methods are particularly useful because they isolate target nucleic acids from a mixture under relatively mild conditions in a short time making them suitable for use in a variety of laboratory and field conditions, or for screening many samples by using manual or automated systems. The target capture compositions and methods are also useful for separating target nucleic acids from a sample which may contain one or more different target nucleic acids, such as those that contain variable or unknown nucleic acid sequences (e.g., different viral types or subtypes, differently spliced RNA transcripts of a gene, or unknown genetic mutants). A nonspecific capture probe as described herein may be used to separate many different genetic subtypes, types, mutants or transcripts from other sample components without requiring design, synthesis, or testing of specific capture probes for each intended target nucleic acid, which may be individually detected, quantified or otherwise treated in subsequent steps on the capture nucleic acids.

A "sample" or "specimen" refers to any composition in which a target nucleic acid may exist as part of a mixture of components, e.g., in water or environmental samples, food stuffs, materials collected for forensic analysis, or biopsy samples for diagnostic testing. "Biological sample" refers to any tissue or material derived from a living or dead organism which may contain a target nucleic acid, including, e.g., cells, tissues, lysates made from cells or tissues, sputum, peripheral blood, plasma, serum, cervical swab samples, biopsy tissues (e.g., lymph nodes), respiratory tissue or exudates, gastrointestinal tissue, urine, feces, semen, or other fluids or materials. A sample may be treated to physically disrupt tissue and/or cell structure to release intracellular components into a solution which may contain enzymes, buffers, salts, detergents and other compounds, such as are used to prepare a sample for analysis by using standard methods.

"Nucleic acid" refers to a multimeric compound comprising nucleotides or analogs that have nitrogenous heterocyclic bases or base analogs linked together to form a polymer, including conventional RNA, DNA, mixed RNA-DNA, and analogs thereof. A nucleic acid includes a "backbone" that links nucleotide monomers, which may be made up of a variety of linkages or conformations, including sugar-phosphodiester, phosphorothioate or methylphosphonate linkages, peptide-nucleic acid linkages (PNA; Nielsen et al., 1994, Bioconj. Chem. 5(1): 3-7; PCT No. WO 95/32305), locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11(7):935-8), or combinations of such linkages in a nucleic acid strand. Sugar moieties of a nucleic acid may be ribose, deoxyribose, or similar compounds, e.g., with 2' methoxy or 2' halide substitutions. Nitrogenous bases may be conventional DNA or RNA bases (A, G, C, T, U), base analogs, e.g., inosine, 5-nitroindazole and others (The Biochemistry of the Nucleic Acids 5-36, Adams et al., ed., 11$^{th}$ ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxygaunosine, -4-ethyl-2'-deoxycytidine (Nguyen et al., 1998, Nucl. Acids Res. 26(18):4249-58), 4,6-difluorobenzimidazole and 2,4-difluorobenzene nucleoside analogues (Klopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; PCT No. WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.). Nucleic acids may include one or more "abasic" residues, i.e., the backbone includes no nitrogenous base for one or more positions (U.S. Pat. No. 5,585,481). A nucleic acid may include only conventional RNA or DNA sugars, bases and linkages, or may include both conventional components and substitutions (e.g., conventional RNA bases with 2'-O-methyl linkages, or a mixture of conventional bases and analogs). Embodiments that may affect stability of a hybridization complex include oligomers that include PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates).

"Oligomer" or "oligonucleotide" refers to a nucleic acid that is generally less than 1,000 nucleotides (nt) long, including those in a size range having a lower limit of about 2 to 5 nt and an upper limit of about 500 to 900 nt. Some preferred oligomer embodiments are in a size range with a lower limit of about 5 to 15 nt and an upper limit of about 50 to 600 nt, whereas other preferred embodiments are in a size range with a lower limit of about 10 to 15 nt and an upper limit of about 18 to 100 nt. Oligomers may be purified from naturally occurring sources, but preferably are synthesized by using any well known enzymatic or chemical method. An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U and G) in a defined portion of a larger oligomer. The resulting oligomer is actually a population of oligomers whose finite number of members is determined by the length and number of bases making up the random portion (e.g., $2^6$ oligomers in a population of oligomers that contains a 6-nt random sequence synthesized by using 2 different bases).

"Capture probe", "capture oligonucleotide", or "capture oligomer" refers to a nucleic acid oligomer that binds nonspecifically to a target nucleic acid by using a sequence that exhibits alternative base pairing properties relative to standard DNA or RNA and joins the captured target nucleic acid to a support for separation of the captured nucleic acid from a solution phase. The capture probe may be joined directly or indirectly to the support to join the capture target nucleic acid to the support. Preferred capture probe embodiments use base pairing of one or more non-random or random polymer portions to a target nucleic acid and a specific binding partner (SBP) to join the capture probe to an immobilized probe attached to a support. The SBP may be joined directly and contiguously to a polymer portion of the capture probe, or may be joined via a non-nucleotide linker to a capture probe sequence. An "immobilized probe" is attached to a support and contains a specific binding partner (SBP') that binds specifically to the SBP of the capture probe, i.e., the SBP and SBP' are members of a specific binding pair. Preferred capture probe embodiments include a random polymer portion made up of one or more poly-(k) segments, in which k is G or T/U in a random sequence. Preferred capture probe embodiments may include an oligonucleotide sequence that serves as the SBP and which is partially or fully complementary to an oligonucleotide sequence of the immobilized probe, i.e., SBP and SBP' are fully or partially complementary sequences.

Specific binding partners are members of a "specific binding pair" or "specific binding partner set" which are able to recognize and bind specifically to each other. Specific binding pairs include, for example, members that are receptor and ligand, enzyme and substrate, enzyme and cofactor, enzyme and coenzyme, antibody and antigen, sugar and lectin, biotin and avidin or streptavidin, ligand and chelating agent, nickel and histidine, completely or substantially complementary nucleic acid sequences, including complementary homopolymeric nucleic acid sequences. Components of a binding partner set are the regions of the members that participate in binding. Members of a specific binding pair may be represented by the abbreviations SBP and SBP'.

An "Immobilized probe", "immobilized oligomer" or "immobilized nucleic acid" refers to a specific binding partner (SBP') that binds specifically to a capture probe's SBP and is attached to a support. That is, the SBP' and SBP bind specifically to join the capture and immobilized probes linked to the support. Some embodiments of an immobilized probe are oligonucleotides that contain a sequence that is fully or partially complementary to a capture probe sequence. The complex that includes the immobilized probe and the capture probe facilitates separation of a target nucleic acid bound to the capture probe from other sample components that are not bound to the capture probe, the immobilize probe, and the support. Any support may be used (e.g., matrices or particles in a solution phase), and the support may be made up of any of a variety of known materials (e.g., nylon, nitrocellulose, glass, polyacrylate, polyacrylamide, mixed polymers, polystyrene, silane polypropylene, and metal). Preferred supports are magnetically attractable particles, e.g., monodisperse paramagnetic beads (uniform size ±5%) to which an immobilized probe is joined stably and directly (via covalent linkage, chelation, or ionic interaction) or indirectly (via a linker).

"Separating", "purifying" or "isolating" refers to selectively removing one or more components of a sample from one or more other sample components, e.g., removing nucleic acids from a generally aqueous solution that also may contain proteins, carbohydrates, lipids, cellular debris, organelles, or inorganic matter. In preferred embodiments, purifying removes at least about 30% of the target nucleic acid, more preferably removes at least about 50% of the target nucleic acid, and even more preferably, removes at least about 75% of the target nucleic acid from other sample components. Alternatively, purifying may be viewed as removing at least about 75% of other sample components, more preferably removing at least about 85% of other sample components, and even more preferably, removing at least about 90% of other sample components from the target nucleic acid.

"Hybridization conditions" refer to the cumulative physical and chemical conditions under which nucleic acid sequences that are completely or partially complementary form a hybridization duplex or complex. Such conditions are well known to those skilled in the art, are predictable based on sequence composition of the nucleic acids involved in hybridization, or may be determined empirically by using routine testing (e.g., Sambrook et al., Molecular Cloning, A Laboratory Manual, $2^{nd}$ ed. (Cold Spring Harbor Laboratory Press, Cold Spring Harbor, NY, 1989) at §§ 1.90-1.91, 7.37-7.57, 9.47-9.51, 11.12-11.13, and 11.45-11.57).

"Sufficiently complementary" means that a contiguous nucleic acid sequence is capable of hybridizing to another sequence by hydrogen bonding between the complementary bases (e.g., G:C, A:T or A:U pairing). Complementary sequences may be complementary at each position in an oligomer sequence relative to its target sequence by using standard base pairing or sequences may contain one or more positions that are not complementary, including abasic residues, but such sequences are sufficiently complementary because the entire oligomer sequence can hybridize with its target sequence in appropriate hybridization conditions. "Nucleic acid amplification" refers to any well known in vitro procedure that produces multiple copies of a target nucleic acid sequence, or its complementary sequence, or fragments thereof (i.e., an amplified sequence containing less than the complete target nucleic acid). Examples of such procedures include transcription associated methods, e.g., transcription-mediated amplification (TMA), nucleic acid sequence-based amplification (NASBA) and others (U.S. Pat. Nos. 5,399,491, 5,554,516, 5,437,990, 5,130,238, 4,868,105, and 5,124,246), replicase-mediated amplification (U.S. Pat. No. 4,786,600), polymerase chain reaction (PCR) (U.S. Pat. Nos. 4,683,195, 4,683,202, and 4,800,159), ligase chain reaction (LCR) (EP Pat. App. 0320308), and strand-displacement amplification (SDA) (U.S. Pat. No. 5,422,252).

"Detection probe" refers to a nucleic acid oligomer that hybridizes specifically under hybridization conditions to a target sequence to allow detection of the target nucleic acid, directly (i.e., probe hybridized directly to the target sequence) or indirectly (i.e., probe hybridized to target via an intermediate structure). A detection probe may include target-binding sequences and other components that contribute to its structure (U.S. Pat. Nos. 5,118,801, 5,312,728, 6,835,542, and 6,849,412).

"Label" refers to a moiety or compound that is detected or leads to a detectable signal, which may be joined directly or indirectly to a detection probe or to the nucleic acid to be detected. Labels joined directly may use covalent bonds or non-covalent interactions (e.g., hydrogen bonding, hydrophobic or ionic interactions, chelate or coordination complex formation) and labels joined indirectly may use a bridging moiety or linker (e.g., antibody or oligomer). A label may be any detectable moiety, e.g., radionuclide, ligand, enzyme, enzyme substrate, reactive group, chromophore (e.g., dye or particle that imparts color), luminescent (bioluminescent, phosphorescent or chemiluminescent) compound, and fluorescent compound. Preferred labels provide a detectable signal in a homogeneous assay, i.e., without requiring separation of unbound label from bound label for signal detection (U.S. Pat. Nos. 5,283,174, 5,656,207 and 5,658,737). Preferred homogeneous detectable labels are chemiluminescent compounds, more preferably acridinium ester (AE) compounds (U.S. Pat. Nos. 5,656,207, 5,658,737, and 5,639,604). Methods of synthesizing labels, attaching labels to nucleic acids, and detecting signals from labels are well known (e.g., Sambrook et al., Molecular Cloning, A Laboratory Manual, 2nd ed., Chapt. 10, and U.S. Pat. Nos. 5,658,737, 5,656,207, 5,547,842, 5,283,174, and 4,581,333).

Unless defined otherwise, technical terms used herein have the same meaning as commonly understood by those skilled in the art or in definitions found in technical literature, e.g., Dictionary of Microbiology and Molecular Biology, 2nd ed. (Singleton et al., 1994, John Wiley & Sons, New York, NY), The Harper Collins Dictionary of Biology (Hale & Marham, 1991, Harper Perennial, New York, NY), and similar publications. Unless described otherwise, techniques employed or contemplated herein are standard well known methods.

In contrast to the nonspecific target capture methods disclosed herein, a specific target capture method uses a capture probe that contains a sequence that hybridizes specifically to a target sequence in the target nucleic acid (e.g., see U.S. Pat. Nos. 6,110,678, 6,280,952, and 6,534,273). Briefly, the specific target capture method uses a capture probe made up of a target-specific sequence that hybridizes specifically to a target sequence in the target nucleic acid and a tail region that hybridizes to the immobilized probe. The specific target capture method uses a two-step hybridization in which the first hybridization condition favors a solution-phase hybridization of the capture probe's target-specific sequence to the target sequence, and then a second hybridization condition that maintains the complex of the capture probe:target nucleic acid and allows hybridization of the capture probe's tail region to an immobilized probe on a support, forming on the support a complex made up of the immobilized probe, capture probe and target nucleic acid. The support and attached complex are separated from the other sample components that remain in the solution phase.

Nonspecific target capture methods described herein make use of a capture probe that hybridizes nonspecifically to target nucleic acid in a sample by using alternative base pairing properties of a portion of the capture probe (compared to standard DNA or RNA hydrogen bonding). The capture probe is attached to a support, preferably by binding specifically to an immobilized probe on the support, which allows the complex that contains the nonspecific capture probe and target nucleic acids to be separated from other sample components. Preferred capture probe embodiments used in the method contain a non-random or random polymer sequences attached to a specific binding partner (SBP). The polymer sequence hybridizes nonspecifically to the target nucleic acid and the SBP binds to a specific binding partner (SBP'), which may be attached to an immobilized probe or to the support. Some embodiments of nonspecific capture probes include a random polymer sequence made up of all four standard DNA bases (guanine (G), cytosine (C), adenine (A) and thymine (T)) or all four standard RNA bases (G, C, A, and uracil (U)). Some embodiments include one or more base analogs (e.g., inosine, 5-nitroindole) or abasic positions in the random polymer sequence. Preferred embodiments include a random polymer sequence that contains one or more sequences of poly-(k) bases, i.e., a random mixture of G and U or T bases (e.g., see WIPO Handbook on Industrial Property Information and Documentation, Standard ST.25 (1998), Table 1). Sequences that include G and U/T bases were chosen for their "wobble" property, i.e., U/T binds G or A, whereas G binds C or U/T. It is understood that a nonspecific capture probe synthesized with a random polymer sequence is in fact a finite population of oligonucleotides that contain different random polymer sequences made up of the bases included during the synthesis of the random portion. For example, a population of nonspecific capture probes that include a 15 nt random polymer sequence made up of G, C, A and T consists of $4^{15}$ members.

The nonspecific capture probes described herein may exist in many different embodiments, but generally they may be represented by the structures, RP-SBP or SBP-RP, in which "RP" stands for the "random polymer" sequence portion and "SBP" stands for the "specific binding partner." In these representational diagrams, the SBP is represented in a linear manner relative to the RP, but those skilled in the art will appreciate that the SBP may be joined at any point to the RP of the capture probe. In embodiments in which the RP is made up of G and U or T bases, the nonspecific capture probe may be represented by the diagramed structures.

$(k)_x$-SBP or SBP-$(k)_x$, in which "k" stands for the G and U or T bases of the RP portion, "x" stands for the length (in nt) of the k sequence, and "SBP" stands for the "specific binding partner." Although the SBP and $(k)_x$ sequences are shown in a linear manner, it will be understood that the SBP may be joined at any point to the capture probe.

The SBP component of a nonspecific capture probe may be any member of a specific binding pair that binds specifically to the SBP' which may be part of an immobilized probe. Some embodiments of specific binding pairs suitable for use as SBP and SBP' members include receptor and ligand pairs, enzyme and substrate or cofactor pairs, enzyme and coenzyme pairs, antibody (or antibody fragment) and antigen pairs, sugar and lectin pairs, biotin and avidin or streptavidin, ligand and chelating agent pairs, nickel and histidine, and completely or substantially complementary nucleic acid sequences. Some preferred embodiments of the target capture method use as the SBP and SBP' members substantially complementary nucleic acid sequences, more preferably complementary homopolymeric sequences, e.g., a capture probe includes a 3' substantially homopolymeric SBP sequence that hybridizes to a complementary immobilized SBP' sequence linked to a support. Other preferred embodiments use as the SBP and SBP' members, non-nucleic acid binding pairs, such as biotin that binds specifically with avidin or streptavidin.

Embodiments of nonspecific capture probes may be synthesized to include any of a variety of nucleic acid conformations, such as standard DNA or RNA oligonucleotides, or oligonucleotides that include one or more modified linkages in which the sugar moieties have substitutions (e.g., 2' methoxy or 2' halide), or one or more positions in alternative conformations, e.g., locked nucleic acid (LNA) or protein nucleic acid (PNA) conformation. A capture probe embodiment may include non-nucleotide compounds as spacers (e.g., C-9) that join random polymer segments of the capture probe. Preferred embodiments of nonspecific capture probes include those in which a random polymer portion is synthesized using 2'-methoxy substituted RNA residues or containing one or more residues in LNA conformation. The choice of conformation(s) to include in oligonucleotide portions of a nonspecific capture probe may depend on the intended target nucleic acid to be isolated. For example, a nonspecific capture probe synthesized in the random polymer region with 2'-methoxy substituted RNA residues is preferred to capture of RNA targets, whereas one synthesized with some LNA conformation in the random polymer region is preferred to capture single-stranded DNA (ssDNA) targets. Some preferred embodiments of capture probes include combinations of conformations (e.g., LNA and DNA).

Nonspecific target capture methods are relatively fast and simple to perform, requiring usually less than an hour to complete, with the target capture reaction requiring as little as 5 minutes of incubation. Optional steps such as washing of the captured nucleic acid to further purify the nucleic acid may be included but require additional time (e.g., about 20 minutes). Nonspecific target capture involves mixing a sample containing a target nucleic acid with a nonspecific capture probe, as described herein, in a substantially aqueous solution and conditions that allow the capture probe to hybridize nonspecifically to the target nucleic acid in the mixture. Such conditions may involve elevated temperatures for a short time (e.g., 60° C. for about 15 min) followed by incubation at room temperature (e.g., about 20-25° C. for about 10 to 90 min), although the entire incubation may be a room temperature and substantially shorter (e.g., 5 min). The mixture may also contain an immobilized probe that binds specifically to the nonspecific capture probe via the SBP-SBP' specific binding pair. The immobilized probe may be introduced into the mixture simultaneously with the capture probe, or before or after the capture probe is mixed with the sample. In some preferred embodiments, the immobilized probe is introduced into the mixture of the sample and the nonspecific capture probe after the capture probe has been incubated with the sample to allow the capture probe and the target nucleic acids to hybridize nonspecifically in solution phase before the capture probe binds with the immobilized probe. In other preferred embodiments, the immobilized probe is introduced into the mixture substantially simultaneously with the capture probe to minimize mixing steps, which is particularly useful for automated systems. In an embodiment that uses a capture probe with a tail sequence as the SBP, the capture probe binds specifically to a complementary sequence (SBP') that is contained in the immobilized probe under nucleic acid hybridizing conditions to allow the target nucleic acid bound nonspecifically to the capture probe and linked to the support via the immobilized probe to be separated from other sample components. Following incubation in which the capture hybridizes nonspecifically to the target nucleic acid and binds specifically to the immobilized probe, the complex made up of the immobilized probe, capture probe and target nucleic acid is separated from other sample components by separating the support with the attached complex from the solution phase. Then, optionally washing step(s) may be performed to remove non-nucleic acid sample components that may have adhered to the complex, a component of the complex, or the support. In preferred embodiments, a washing step is performed in which the complex attached to the support is washed with a substantially aqueous wash solution that maintains the hybridization complex on the support and then the complex attached to the support is separated from the washing solution which contains the other sample components. The captured target nucleic acid may be separated from one or more of the other complex components before subsequent assay steps are performed, or the complex attached to the support may be used directly in a subsequent step(s). Subsequent steps include, e.g., detection of the captured nucleic acid and/or in vitro amplification of one or more sequences contained in the captured nucleic acid.

Based on the nonspecific capture probes designed and tested under a variety of conditions, the following general conclusions about nonspecific target capture using these compositions have been drawn. Nonspecific capture probes that include randomized G and U bases are more effective at target capture than those that include a nonrandom repeating (GU) sequence that totals the same number of nucleotides as in the random G/U polymer portion. Nonspecific capture probes that include randomized poly-(k) sequences synthesized by using 2'-methoxy RNA bases are more effective at target capture than those of similar structure synthesized by using deoxy linkages. Nonspecific capture probes that include randomized poly-(k) sequences are more effective at target capture than those that include a randomized DNA segment (randomized G, A, T and C bases) in the random polymer portion. Nonspecific capture probes that include randomized poly-(k) sequences are more effective at target capture than those that include a similar length of poly-inosine, poly-U, or randomized C and A bases (i.e., poly-(m) sequences) in the probe. Although the length of one or more contiguous random sequences contained in a nonspecific capture probe may vary, a poly-(k) sequence of about 12 nt or greater is sufficient for efficient target capture. The presence of non-random oligonucleotide or non-nucleotide spacers between random poly-(k) sequences in a nonspecific capture probe may affect target capture efficiency. Nonspecific capture probes that include at least part of a random poly-(k) sequence in LNA conformation are more effective at ssDNA target capture than a nonspecific capture probe of similar length in DNA conformation, and those that contain a mixture of LNA and DNA residues are more effective than those that contain all poly-(k) sequences in LNA conformation. Nonspecific capture probes that include at least part of a random poly-(k) sequence in LNA conformation are more effective at target capture of RNA and ssDNA than target capture of double-stranded DNA (dsDNA). Nonspecific capture probes that include at least part of a random poly-(k) sequence in LNA conformation are more effective at RNA target capture than capture probes in which the same length of random poly-(k) sequence is synthesized by using 2'-methoxy RNA bases. These general parameters may be used to design and optimize embodiments of nonspecific capture probes for capture of an intended target nucleic acid or type of target nucleic acid which may be tested by using standard procedures as described in the examples that follow to select a nonspecific capture probe and conditions that provide the desired target capture results.

An immobilized probe may be connected to a support by any linkage that is stable in the hybridization conditions used in the target capture method. Preferred embodiments use a support of monodisperse particles which can be retrieved from solution by using known methods, e.g., centrifugation, filtration, magnetic attraction, or other physical or electrochemical separation. The captured target nucleic acid is isolated and concentrated on the support, i.e., target nucleic acid is concentrated on the support compared to its concentration in the initial sample, which may improve sensitivity of subsequence assay steps performed using the captured nucleic acids.

Target capture methods described herein may be used to isolate two or more target nucleic acids from the same sample simultaneously because the nonspecific capture probe binds to more than one species of nucleic acid present in a sample. In some embodiments, nonspecific capture probes may be designed and selected for use to preferentially capture a particular type of nucleic acid (e.g. RNA) from a sample that contains a mixture of nucleic acids (e.g., DNA and RNA). In some embodiments, nonspecific capture probes may be selectively removed from a mixture by designing the capture probes to selectively bind to different immobilized probes which are introduced into the mixture and then separated with an attached complex containing the capture probe and the target nucleic acid. For example, a first nonspecific capture probe that binds preferentially to RNA in a DNA and RNA mixture may bind via a first SBP to a first immobilized SBP' on a first support and a second nonspecific capture probe that binds preferentially to DNA in a DNA and RNA mixture may bind via a second SBP to a second immobilized SBP' on a second support. Then, by selectively removing the first and second supports with their attached complexes to different regions of an assay system or at different times during an assay, the RNA components of a sample may be selectively separated from DNA components of the same sample. Methods for determining optimal nonspecific capture probe structures and conditions for their use are described in the examples that follow.

Model systems were used to test the efficiency of nonspecific target capture by using a variety of different capture probes and different conditions for the capture of RNA (*Chlamydia trachomatis* rRNA) and DNA (synthetic oligonucleotides) target nucleic acids. In a typical test, a sample was prepared by mixing the target nucleic acid labeled with a detectable marker (e.g., a labeled probe) at a known concentration with a substantially aqueous solution (e.g., a buffered solution containing salts and chelating agent). A portion of the sample was mixed with a reagent that contained in a substantially aqueous solution a known amount of the nonspecific target capture probe to be tested and a known amount of immobilized probe attached to a support (e.g., a magnetic particle) to make a target capture mixture. The target capture mixture was incubated at predetermined temperature(s) for predetermined time(s) to allow formation of a capture complex made up of the nonspecific capture probe, the target nucleic acid, and the immobilized probe attached to the support. The complex on the support was then separated from the solution phase. The complex on the support optionally was washed to remove remaining portions of the solution phase, and the complex on the support was separated from the washing solution. The label associated with the support was detected to provide a measurement of the efficiency of the target capture, i.e., to provide a quantitative measurement of the amount of target nucleic acid that was separated from the other sample components. The label associated with the solution phase that had been initially separated from the complex on the support was also detected to provide a measurement of the labeled target nucleic acid that was still present in the solution phase following the target capture step. Although the model systems were designed to contain a minimum of components so that the different nonspecific capture probes and conditions could be compared, it will be understood that additional oligonucleotides, such as helper oligonucleotides (U.S. Pat. No. 5,030,557, Hogan et al.) and/or amplification primers may be included in a target capture mixture.

In some cases, for comparison, samples were subjected to target capture by using a specific target capture probe that hybridizes specifically to the target nucleic acid, by using a known process that uses a first incubation that allows hybridization of the specific capture probe to its target nucleic acid, and then a second incubation that allows hybridization of an immobilized oligonucleotide probe to a complementary sequence in the specific capture probe (U.S. Pat. No. 6,110,678, Weisburg et al.). Typically, the specific target capture process mixes a sample that contains the target nucleic acid labeled with a detection probe, with a capture probe (e.g., 1.75 pmoles) that hybridizes specifically with the target nucleic acid and about 100 µg of immobilized probe attached to paramagnetic particles (e.g., $dT_{14}$ probes attached to 0.7-1.05µ magnetic particles (Seradyne) by using carbodiimide chemistry (Lund, et al., 1988, Nuc. Acids Res. 16:10861-10880)), then incubates the mixture at 55-60° C. for about 15-30 min and then at room temperature for 5-15 min to allow sequential hybridization of the capture probe and target nucleic acid and then of the immobilized probe to the capture probe:target nucleic acid complex. Application of a magnetic field separates particles with attached complexes from the solution phase at a portion of the container (U.S. Pat. No. 4,895,650), and the supernatant is removed. Particles are suspended in a wash solution (e.g., 1 ml at room temperature) and the magnetic separation step is repeated.

Nonspecific target capture probes were synthesized using standard in vitro methods which are well known in the art (Caruthers et al., Methods in Enzymology, vol. 154, p. 287 (1987); U.S. Pat. No. 5,252,723, Bhatt; WO 92/07864, Klem et al.). The synthesized oligonucleotides were made using standard RNA bases and linkages, DNA bases and linkages, RNA bases with 2' methoxy linkages, DNA bases in LNA conformation, or in oligonucleotides that contain a combination of such structures. Some oligonucleotides were synthesized to include non-nucleotide spacers (e.g., C-9) or nucleic acid analogues (e.g., inosine or 5-nitroindole). The nonspecific portions of the capture probe typically contained one or a series of positions that were random "k" residues, i.e., G or U for RNA bases, or G or T for DNA or LNA bases. Unless otherwise indicated, random k residues were synthesized by using a mixture that contained equal amounts of G and U bases, or G and T bases. Many embodiments of the nonspecific capture probes included a 5' portion that contained the nonspecific sequences that hybridize nonspecifically to a target nucleic acid and a 3' DNA "tail" sequence, typically made up of $dT_3dA3o$ or $dA_{30}$ sequence. The tail portion is complementary to poly-dT oligomers attached to the support, so that the capture probe (with or without bound target nucleic acid) becomes associated with the support and is separated from the solution phase of a target capture mixture. It will be understood that any "tail" sequence or non-nucleic acid specific binding partner (SBP) may be attached to a nonspecific capture probe, and the chosen specific binding partner on the support (SBP') is a member of a specific binding pair with the SBP.

Embodiments of the nonspecific capture probes described herein use the following nomenclature to abbreviate the structure of the oligonucleotide components in a 5' to 3' orientation. An oligonucleotide that contains one or more residues of random G or U/T bases uses the term "$(k)_x$," where "k" stands for the random assortment of G and U of G and T, and "x" designates the number of positions in the random assortment of G and U of G and T bases. If the oligonucleotide uses a standard RNA backbone, the term may also include "r" to designate RNA for the random assortment of G and U bases, e.g., $r(k)_x$, whereas if the oligomer uses RNA bases with a backbone of 2'-methoxy linkages, the term may also include "2'-Omer" to designate the modified linkages of the random assortment of G and U bases, e.g., 2'-Ome-$(k)_x$. If the oligonucleotide uses standard DNA linkages, the term may include "d" to designate DNA for the random assortment of G and T bases, e.g., $d(k)_x$, whereas if the oligomer uses DNA bases with a locked nucleic acid (LNA) conformation, the term includes "L" to designate the LNA conformation for the random assortment of G and T bases, e.g., $L(k)_x$. An oligonucleotide made up of a combination of different portions may include one or more of these terms to define the entire structure. For example, an oligonucleotide made up of six random G and T bases (k bases) with standard DNA linkages, three T bases with standard DNA linkages, and five random G and T bases (k bases) with standard DNA linkages in a 5' to 3' orientation would be abbreviated as $d(k)_6$-$dT_3$-$d(k)_5$. For another example, an oligonucleotide in a 5' to 3' orientation made up of five random G and T bases with LNA linkages, three A bases with DNA linkages, and four random G and T bases with DNA linkages would be abbreviated as $L(k)_5$-$dA_3$-$d(k)_4$. For another example, an oligonucleotide in a 5' to 3' orientation made up of ten random G and U bases with 2'-methoxy linkages and a 3' tail of fifteen A bases with standard DNA linkages would be abbreviated as 2'-Ome-$(k)_{10}$-$dA_{30}$.

In a few cases, synthesized oligonucleotides of relatively complicated structures were tested by determining the actual molecular weight of the synthesized oligonucleotides compared to the predicted molecular weight (M.W.) of the oligonucleotide based on the intended structure. For example, two different batches of oligonucleotides synthesized to produce a structure of $L(k)_4$-$d(k)_3$-$L(k)_4$-$d(k)_3$-$L(k)_4$-$dT_3dA_{30}$ (SEQ ID NO:18), which has a predicted M.W. of 16308 D, were found to have M.W. of 16263 D and 16248 D. The slightly smaller measured M.W. imply that a few oligonucleotides in the population have predominantly T rather than a T/G mixture.

Relative efficiencies of the target capture probes and conditions were determined by measuring the signal produced from detection probes bound to the captured target after the complex that included the capture probe, target nucleic acid, and immobilized probe attached to the support was separated from the mixture. Although a detection probe may be attached to the target nucleic acid at any point, for convenience and consistency of labeling the target nucleic acid in the sample in the model systems tested, the detection probe was specifically hybridized to the target nucleic acid during the process of making the samples. Those skilled in the art will also appreciate that the capture target nucleic acid may be detected by using other standard methods of detecting nucleic acids, e.g., by binding a dye to the target nucleic acid, before or after capture, or incorporating a detectable label directly into a target nucleic acid (e.g., a radioactive label).

Based on the results obtained using different capture probes with different target nucleic acids in the model systems, the nonspecific capture probes performed at different efficiencies under the same conditions, thus demonstrating that the structure of a nonspecific capture probe may affect its relative affinity for a particular type of target nucleic acid. Based on those observations, one skilled in the art may design and optimize a target capture probe to bias the efficiency of a capture reaction to select for a certain type of target nucleic acid, e.g., to bias the reaction to preferentially capture a DNA target instead of an RNA target. By using methods described herein, one skilled in the art may design a variety of different but structurally-related nonspecific capture probes and test them to optimize a capture reaction for efficient capture of a particular type of target nucleic acid.

Examples are included to describe embodiments of the disclosed nonspecific target capture methods and compositions. Reagents commonly used in assays described below are as follows, although those skilled in the art of molecular biology will appreciate that many different reagents are available to perform the basic steps of the reactions and tests described. Sample transport reagent: 110 mM lithium lauryl sulfate (LLS), 15 mM $NaH_2PO_4$, 15 mM $Na_2HPO_4$, 1 mM EDTA, 1 mM EGTA, pH 6.7. Target capture reagent (TCR): 250 mM HEPES, 1.88 M LiCl, 310 mM LiOH, 100 mM EDTA, pH 6.4, and 250 µg/ml of paramagnetic particles (0.7-1.05µ particles, Sera-Mag™ MG-CM) with $(dT)_{14}$ oligomers covalently bound thereto. Wash solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Hybridization reagent: 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7. Selection reagent: 600 mM boric acid, 182.5 mM NaOH, 1% (v/v) octoxynol (TRITON® X-100), pH 8.5 or pH 9.2, to hydrolyze AE labels on unhybridized detection probe oligomers.

Detection reagents comprise Detect reagent I: 1 mM nitric acid and 32 mM $H_2O_2$, and Detect reagent II: 1.5 M NaOH, to produce chemiluminescence from AE labels (see U.S. Pat. Nos. 5,283,174, 5,656,744, and 5,658,737).

Captured target nucleic acids may be detected by using any process that detects nucleic acids, which are well known to those skilled in the art of molecular biology. For example, the captured nucleic acids may be detected by using dyes that bind selectively to nucleic acids in general or selectively to a particular form of nucleic acid. Specific nucleic acids may be detected by binding a detection probe that hybridizes specifically to a target sequence in a captured nucleic acid, or target sequences in the captured nucleic acids may be treated by in vitro nucleic acid amplification to amplify part of the captured nucleic acid which then is detected. In the model systems described in the examples, the target nucleic acid in the sample was generally labeled before target capture by hybridizing it to a specific detection probe that was labeled with an acridinium ester (AE) compound that produced a chemiluminescent signal (expressed as relative light units or "RLU") in a homogeneous system by using well known procedures described in detail elsewhere (U.S. Pat. No. 5,658,737, see column 25, lines 27-46, and Nelson et al., 1996, Biochem. 35:8429-8438 at 8432).

Example 1: Nonspecific Target Capture of RNA

This example demonstrates the efficiency of various nonspecific target capture probe to capture RNA. Tests were performed by using a known amount of *Chlamydia trachomatis* rRNA (a mixture of 16S and 23S rRNA) which was hybridized to a labeled detection probe complementary to a sequence in the rRNA to label the target rRNA before it was captured. Typically, to prepare the test samples, 200 fmole of rRNA was hybridized with 1 pmole of a AE-labeled oligonucleotide in hybridization reagent (60° C. for 60 min in 0.04 ml), and then cooled to room temperature (RT) and diluted with 0.3 ml of hybridization reagent. An aliquot (10 μl) of the probe-labeled target nucleic acid mixture was mixed with 0.5 ml of a substantially aqueous solution (made up of 0.2 ml sample transport reagent, 0.2 ml water and, 0.1 ml of TCR containing 50 μg of magnetic particles with poly-dT immobilized probes) and 20 pmoles of the nonspecific capture probe. The mixture was incubated to allow attachment of the nonspecific capture probe to the target nucleic acid and hybridization of the 3' tail portion of the nonspecific capture probe to the complementary immobilized probe. The magnetic particles were separated from the solution phase by application of a magnetic field to the outside of the reaction vessel (pellet portion), and the supernatant portion was removed and saved. The magnetic particles with attached complexes in the pellet portion were optionally washed (1 ml of Wash solution at RT) and pelleted as before from the wash solution. The magnetic particles with attached complexes in the pellet portion were suspended in 0.1 ml of a buffered aqueous solution and 0.1 ml of the saved supernatant portion was mixed separately with 50 μg of magnetic particles to make a comparable supernatant aliquot for signal detection. A selection reagent (0.2 ml) was added to both the pellet and supernatant samples which were incubated at 60° C. for 10 min for hydrolysis of the AE label on detection probes not bound to the target nucleic acid. Then detection reagents were added sequentially to produce chemiluminescence from the remaining AE labels on probes bound to the target nucleic acid and the relative light unit (RLU) signals were measured in a luminometer (LEADER®, Gen-Probe Incorporated), substantially as described previously (U.S. Pat. Nos. 5,283, 174 and 5,656,744, Arnold et al., and U.S. Pat. No. 5,658, 737, Nelson et al., at column 25, lines 27-46; Nelson et al., 1996, Biochem. 35:8429-8438 at 8432).

In a first set of tests, the nonspecific capture probes had a 5' nonspecific target-capture sequence made of RNA bases and 2'-methoxy linkages and a 3' DNA tail sequence of $dT_3dA_3o$, as shown by the structures:

$(n)_6$-$U_3$-$(n)_6$-$dT_3dA_{30}$ (SEQ ID NO:1), $(n)_6$-$Ni_5$-$(n)_6$-$dT_3dA_{30}$ (SEQ ID NO:2) in which "Ni" stands for 5-nitroindole, and $(k)_6$-$Ni_5$-$(k)_6$-$dT_3dA_{30}$ (SEQ ID NO:3) in which "Ni" stands for 5-nitroindole.

The target capture tests were performed as described above using incubation at 60° C. for 15 min, followed by RT for 90 min. Negative controls were treated the same but included no target capture probe, and positive controls used a specific target capture probe that included a sequence that hybridized specifically to a target sequence in the probe labeled rRNA as previously described (U.S. Pat. No. 6,110, 678, Weisburg et al.). Table 1 shows the results obtained in these tests, with the detected RLU for the supernatant and pellet portions shown in columns 2 and 3, respectively, and the calculated percentage of target nucleic acid captured in the pellet in column 4. These results show that between the two nonspecific capture probes that contain 5-nitroindole spacers between the randomized hexamers, the probe that contains randomized k hexamers (G/U) captured RNA more efficiently than a nonspecific capture probe that contains randomized n hexamers (G, A, C and U), and the capture that contained randomized n hexamers joined by three U bases captured the target similar to the probe that contains randomized k hexamers.

TABLE 1

| Target Capture Probe | Supernatant RLU | Pellet RLU | % Target Capture |
|---|---|---|---|
| $(n)_6$-$U_3$-$(n)_6$-$dT_3dA_{30}$ | 34332 | 76526 | 34 |
| $(n)_6$-$Ni_5$-$(n)_6$-$dT_3dA_{30}$ | 46052 | 11766 | 5.2 |
| $(k)_6$-$Ni_5$-$(k)_6$-$dT_3dA_{30}$ | 32080 | 84430 | 37.5 |
| Negative Control | 45019 | 5186 | 2.3 |
| Positive Control | 6515 | 225028 | 99.9 |

In a second set of tests, the nonspecific capture probes had a 5' nonspecific target-capture sequence made of RNA bases and 2'-methoxy linkages and a 3' $dT_3dA_{30}$ sequence, as shown by the structures:

$(I)_{12}$-$dT_3dA_{30}$ (SEQ ID NO:4), in which "I" represents inosine, $(k)_6$-C9-C9-$(k)_6$-$dT_3dA_{30}$ (SEQ ID NO:5), in which "C9" stands for a 9 carbon non-nucleotide spacer, and $(k)_6$-C9-$(k)_6$-C9-$(k)_6$-$dT_3dA_{30}$ (SEQ ID NO:6), in which "C9" stands for a 9 carbon non-nucleotide spacer.

The target capture tests were performed as described above except that incubation was 60° C. for 15 min, followed by RT for 60 min. Table 2 shows the results of these tests, shown as described above. These results show that between the two nonspecific capture probes that contain C9 spacers, both the probe with two k hexamers and the probe with three k hexamers efficiently captured the rRNA, but the poly-inosine probe was inefficient at RNA target capture.

TABLE 2

| Target Capture Probe | Supernatant RLU | Pellet RLU | % Target Capture |
|---|---|---|---|
| $(I)_{12}$-$dT_3dA_{30}$ | 54207 | 2890 | 1 |
| $(k)_8$-C9-C9-$(k)_6$-$dT_3dA_{30}$ | 14105 | 209987 | 76 |
| $(k)_6$-C9-$(k)_6$C9-$(k)_6$-$dT_3dA_{30}$ | 7135 | 261263 | 94 |
| Negative Control | 55392 | 3514 | 1.3 |
| Positive Control | 12079 | 227118 | 82 |

In a third set of tests, the C9-containing nonspecific capture probes of SEQ ID Nos. 5 and 6 were tested similarly but performing the incubation at 60° C. for 15 min, followed by RT for 15 min. In those experiments, the efficiency of RNA capture was 32% for capture probe of SEQ ID NO:5 and 50.7% for the capture probe of SEQ ID NO:6, compared to the positive control of 79% capture and the negative control (0% capture).

Example 2: Nonspecific Target Capture of RNA

This example demonstrates efficiencies of nonspecific target capture of rRNA by using a variety of different capture probes in assays performed substantially as described in Example 1 except that the target capture incubations were at RT for 10 to 30 min. All of the nonspecific capture probes used were synthesized using RNA bases and 2'-methoxy linkages and a 3' DNA tail sequence.

In a first set of tests, the C9-containing nonspecific capture probes of SEQ ID Nos. 5 and 6 were tested using incubation at RT for 30 min, and the efficiency of RNA capture was 71% for capture probe of SEQ ID NO:5 and 89.5% for the capture probe of SEQ ID NO:6, compared to the positive control of 53% capture and the negative control of 1.3% capture. These results shown that incubation at 60° C. was not needed for efficient nonspecific target capture of RNA.

In a second set of target captures, also incubated at RT for 30 min, the nonspecific capture probe of SEQ ID NO:5 was compared to three other nonspecific capture probes, having the structures shown as:

$(k)_{12}$-$dT_3dA_{30}$ (SEQ ID NO:7),
$(k)_6$-$U_3$-$(k)_6$-$dT_3dA_{30}$ (SEQ ID NO:8), and
$(k)_6$-$U_6$-$(k)_6$-$dT_3dA_{30}$ (SEQ ID NO:9).

Table 3 shows the results of these tests, shown as described in Example 1. These results show the relative efficiencies of the different nonspecific capture probe designs, all of which captured the target RNA at RT.

TABLE 3

| Target Capture Probe | Supernatant RLU | Pellet RLU | % Target Capture |
|---|---|---|---|
| $(k)_6$-C9-C9-$(k)_6$-$dT_3dA_{30}$ | 15271 | 185379 | 64 |
| $(k)_{12}$-$dT_3dA_{30}$ | 3139 | 247047 | 85 |
| $(k)_6$-$U_3$-$(k)_6$-$dT_3dA_{30}$ | 3527 | 255462 | 88 |
| $(k)_6$-$U_6$-$(k)_6$-$dT_3dA_{30}$ | 11481 | 215427 | 74 |
| Negative Control | 57984 | 3891 | 1.3 |

In a third set of tests, target capture of rRNA was performed using the same nonspecific capture probes (SEQ ID Nos. 5, 7, 8, and 9) but the incubation was performed at RT for 10 min. The results of these tests are shown in Table 4. These results compared to those of Table 3 show that longer incubation at RT provides somewhat greater target capture but significant target capture occurred in as little as 10 min at RT. Comparison of the results of Table 4 for the capture efficiencies of the probe containing $U_3$ linking two k hexamers with the probe containing $U_6$ linking two k hexamers show that the probe with the $U_3$ spacer was more efficient. Based on these and other results, generally a capture probe that includes a shorter spacer (e.g., 3 nt, or a C-9 spacer) was more efficient at target capture than one of similar structure that includes a longer spacer (e.g., 6 nt, or two adjacent C-9 spacers).

TABLE 4

| Target Capture Probe | Supernatant RLU | Pellet RLU | % Target Capture |
|---|---|---|---|
| $(k)_6$-C9-C9-$(k)_6$-$dT_3dA_{30}$ | 26821 | 103257 | 44 |
| $(k)_{12}$-$dT_3dA_{30}$ | 13279 | 177412 | 77 |
| $(k)_6$-$U_3$-$(k)_6$-$dT_3dA_{30}$ | 16782 | 168742 | 73 |
| $(k)_6$-$U_6$-$(k)_6$-$dT_3dA_{30}$ | 24978 | 114631 | 49 |
| Negative Control | 46334 | 2255 | 1 |

Example 3: Target Capture of HIV-1 Target RNA

This example demonstrates the use of two different nonspecific target capture probes to capture HIV-1 sequences, which were synthetic RNA sequences corresponding to portions of the protease-encoding gene of and the RT4 gene of HIV-1. Tests were performed individually for both target nucleic acids by using a known amount of in vitro RNA transcripts prepared from cloned Protease and RT4 sequences (a 681 nt Protease transcript, and a 471 nt RT4 transcript) which were hybridized specifically and individually to a labeled detection probe complementary to a sequence in the target rRNA before it was captured. To prepare the test samples, 200 fmole of the target RNA was hybridized specifically with 1 pmole of a AE-labeled detection probe oligonucleotide in hybridization reagent (60° C. for 60 min in 0.04 ml), cooled to room temperature (RT) and diluted with 0.3 ml of hybridization reagent. An aliquot (10 µl) of the probe-labeled target RNA mixture was mixed with 0.5 ml of a substantially aqueous solution (made up of 0.2 ml sample transport reagent, 0.2 ml water and, 0.1 ml of TCR containing 50 µg of magnetic particles with poly-dT immobilized probes) and 20 pmoles of the nonspecific capture probe. The mixture was incubated at RT for 30 min to allow attachment of the nonspecific capture probe to the target nucleic acid and hybridization of the 3' tail of the capture probe to the immobilized probe. The magnetic particles with attached complexes were separated from the solution phase by application of a magnetic field (pellet portion), and the supernatant portion was saved. The pellet portion was washed (0.5 ml of sample transport reagent at RT) and separated as before to make the pellet portion which was mixed with 0.1 ml of a buffered aqueous solution for detection of RLU. A portion (0.1 ml) of the saved supernatant was mixed with 50 µg of magnetic particles for detection of RLU. To each mixture for detection of RLU, selection reagent (0.2 ml) was added and the mixtures were incubated at 60° C. for 10 min, followed by mixture with detection reagents and detection of chemiluminescence (RLU) as described in Example 1.

The nonspecific capture probes used in these tests were $(k)_{12}$-$dT_3dA_{30}$ (SEQ ID NO:7) and $(k)_6$-C9-$(k)_6$-C9-$(k)_6$-$dT_3dA_{30}$ (SEQ ID NO:6). Negative controls were treated the same as the test samples but the mixtures contained no capture probe. Table 5 shows the results of these tests which demonstrate that both nonspecific capture probes were effective at capturing the HIV-1 target RNA from the mixtures.

TABLE 5

| Target HIV-1 RNA | Measurement | Capture Probes Used | | |
|---|---|---|---|---|
| | | $(k)_{12}$-$dT_3dA_{30}$ | $(k)_6$-C9-$(k)_6$-C9-$(k)_6$-$dT_3dA_{30}$ | None |
| Protease | Supernatant RLU | 1407 | 1876 | 37493 |
| | Pellet RLU | 177632 | 169693 | 460 |
| | % Target Capture | 95 | 91 | 0.24 |
| RT4 | Supernatant RLU | 1993 | 2307 | 86406 |
| | Pellet RLU | 317337 | 329149 | 448 |
| | % Target Capture | 73 | 76 | 0.1 |

Example 4: Kinetics of Target Capture that Uses Nonspecific Capture Probes

This example shows that target capture that uses nonspecific capture probes is efficient at RT, with significant capture occurring in as little as 2-5 min. These tests were performed substantially as described in Example 2, except that incubation was for varying lengths of time (1-60 min) before the pellet portions were isolated and signals (RLU) from the captured target RNA were measured to determine the relative efficiencies of target capture over time.

In a first set of tests, the detection probe-labeled rRNA targets were captured using the following nonspecific capture probes (20 pmoles per reaction), all synthesized with RNA bases and 2'-methoxy linkages in the nonspecific portion and with 3' DNA tails: $(k)_{12}$-$dT_3dA_{30}$ (SEQ ID NO:7), $(k)_{18}$-$dT_3dA_{30}$ (SEQ ID NO:11), and $(k)_{24}$-$dT_3dA_{30}$ (SEQ ID NO:12). The target capture mixtures were incubated at RT for 1, 2, 5, 10 and 20 min before the pellet portions were isolated and signals were measured. In related tests, the same nonspecific capture probes and a $(k)18$ capture probe synthesized with 2'-methoxy RNA groups in the 5' nonspecific portion and a 3' tail containing poly-A residues in a mixture of DNA and LNA conformations (SEQ ID NO:13), as illustrated by $(k)_{18}$-$dT_3dA_3LA_1dA_3LA_1dA_1LA_1dA_1LA_1dA_3LA_1dA_3LA_1dA_1LA_1dA_1LA_2$-$dA_3LA_1dA_1$ which is shortened to $(k)_{18}$-$dT_3$ $d/L(A_{30})$ in Table 6) were tested under the same conditions but incubation was for 18 min. For all of these tests, the negative controls were treated the same as the test samples except that no capture probe was included in the target capture mixture. The negative controls resulted in RLU signals equivalent to 1.4 to 1.9% of the target. The results of these tests are show in Table 6. The results demonstrate that maximal capture was observed after 18-20 min incubation but significant capture was observed after as little as 1-2 min incubation at RT, and the presence of LNA conformation in the 3' tail portion did not improve the efficiency of nonspecific target capture.

In a second set of tests, the same rRNA targets were captured using the same nonspecific capture probes of the first set of tests and another nonspecific capture probe containing a 18-nt portion of random G and T bases, synthesized with 2'-methoxy linkages and a 3' DNA tail, as shown by $(G/T)_{18}$-$dT_3dA_{30}$ (SEQ ID NO:14). The target capture mixtures were incubated at RT for 5 and 60 min before the pellet portions were isolated and signals were measured. The negative control which was treated the same but contained no capture probe provided in the pellet portion 1078 RLU after 5 min incubation and 2160 RLU after 60 min incubation. The results of the tests for the reactions performed with nonspecific capture probes are show in Table 7, which demonstrate that maximal capture was observed after 60 min incubation but significant capture was observed after 5 min incubation at RT.

TABLE 7

| | | Time | |
|---|---|---|---|
| Capture Probe | Measurement | 5 min | 60 min |
| $(G/U)_{12}$-$dT_3dA_{30}$ | RLU | 103680 | 193706 |
| | % Capture | 61 | 90 |
| $(G/U)_{18}$-$dT_3dA_{30}$ | RLU | 102900 | 191273 |
| | % Capture | 60 | 89 |
| $(G/T)_{18}$-$dT_3dA_{30}$ | RLU | 101969 | 171642 |
| | % Capture | 60 | 80 |
| $(G/U)_{2}4$-$dT_3dA_{30}$ | RLU | 92880 | 169655 |
| | % Capture | 54 | 79 |

In a third set of tests, the same rRNA targets were captured using the nonspecific capture probes that have an 18-nt 5' portion synthesized as either random G/U sequences or random G/T sequences, synthesized with 2'-methoxy linkages and a 3' DNA tail. The target capture mixtures were incubated at RT for 0 to 50 min before the pellet portions were isolated and signals were measured. The results of these tests are show in Table 8, which demonstrate that maximal capture was observed after 50 min incubation but

TABLE 6

| | | Incubation Time | | | | | |
|---|---|---|---|---|---|---|---|
| Probe | Detected | 1 min | 2 min | 5 min | 10 min | 18 min | 20 min |
| $(k)_{12}$-$dT_3dA_{30}$ | RLU | 83323 | 102949 | 135301 | 136885 | 221129 | 155244 |
| | % Capture | 46 | 57 | 74 | 75 | 89 | 85 |
| $(k)_{18}$-$dT_3dA_{30}$ | RLU | 88694 | 106381 | 137618 | 149335 | 224517 | 154905 |
| | % Capture | 49 | 59 | 76 | 82 | 90 | 85 |
| $(k)_{18}$-$dT_3d/L(A_{30})$ | RLU | — | — | — | — | 197141 | — |
| | % Capture | — | — | — | — | 79 | — |
| $(k)_{24}$-$dT_3dA_{30}$ | RLU | 88016 | 103390 | 137837 | 142599 | 213887 | 172904 |
| | % Capture | 48 | 57 | 76 | 78 | 86 | 95 | significant capture was observed after 1-2 min incubation at RT, with the capture probe containing random G/T sequences performing slightly more efficiently than the capture probe containing random G/U sequences at all time points.

TABLE 8

| Incubation Time | Capture Probe (G/U)$_{18}$-dT$_3$dA$_{30}$ | | Capture Probe (G/T)$_{18}$-dT$_3$dA$_{30}$ | |
|---|---|---|---|---|
| | RLU | % Target Capture | RLU | % Target Capture |
| 0 min | 1021 | 0.5 | 1021 | 0.5 |
| 1 min | 75862 | 38.8 | 85627 | 43.8 |
| 2 min | 85353 | 43.7 | 111917 | 57.3 |
| 3 min | 100752 | 51.6 | 132576 | 67.9 |
| 5 min | 120336 | 61.6 | 155315 | 79.5 |
| 10 min | 159137 | 81.4 | 195277 | 100 |
| 15 min | 161803 | 82.8 | 196698 | 100 |
| 50 min | 192962 | 98.8 | 194865 | 99.7 |

Example 5: Target Capture Using Different Designs of Nonspecific Capture Probes

This example demonstrates that many different embodiments of nonspecific capture probes are effective at capture of rRNA target nucleic acid and that testing of different capture probes may be used to optimize assay performance. The tests described in this example were performed substantially as described in Example 2 by using detection probe-labeled rRNA as the target and RT incubation of the target capture mixtures.

In a first set of tests, the nonspecific capture probes all contained 3' DNA tails of dT3dA3o but were synthesized with different structures in the 5' nonspecific portion as described in the following structures:

(k)$_{18}$-dT$_3$dA$_{30}$ (SEQ ID NO:11), with 5' portion synthesized with RNA bases and 2'-methoxy linkages, d(k)$_6$-dT$_3$-d(k)$_6$-dT$_3$dA$_{30}$ (SEQ ID NO:10), with 5' portion synthesized as DNA only;

L(k)$_6$-dT$_3$-L(k)$_6$-dT$_3$dA$_3$o (SEQ ID NO:15), with 5' portion synthesized as LNA and DNA; and L(k)$_4$-d(k)$_2$-dT$_3$-L(k)$_4$-d(k)$_2$-dT$_3$dA$_{30}$ (SEQ ID NO:16), with 5' portion synthesized as LNA and DNA. The capture probe of SEQ ID NO:11 was synthesized by using different proportions of G and U bases (50:50, 70:30, and 30:70) to determine if any particular random mixture was preferable for efficient RNA target capture. The target capture mixtures contained separately 20 pmoles of the nonspecific capture probes and were incubated at RT for 20 and then treated as described in Example 2 to determine the signal associated with the pellet portions following target capture. The negative control was treated the same except that the mixture contained no capture probe and provided 38267 RLU in the supernatant portion and 1379 RLU in the pellet portion. The results of these tests are shown in Table 9, which demonstrate that different conformations of nonspecific capture probes function at different relative efficiencies. Capture probes with random assortments of G and U bases synthesized with G:U=50:50 or 30:70 were more effective than those synthesized with G:U=70:30 (compare rows 2 to 4 of Table 9). Capture probes of similar structure but made with LNA residues were more effective than the corresponding capture probes with DNA residues (compare rows 5 and 6 in Table 9).

TABLE 9

| Capture Probe | 5' Nonspecific Portion | RLU in Pellet | % Capture |
|---|---|---|---|
| (k)$_{18}$-dT$_3$dA$_{30}$ | k is G:U = 50:50 | 135891 | 71 |
| (k)$_{18}$-dT$_3$dA$_{30}$ | k is G:U = 70:30 | 78865 | 41 |
| (k)$_{18}$-dT$_3$dA$_{30}$ | k is G:U = 30:70 | 136066 | 71 |
| d(k)$_6$-dT$_3$-d(k)$_6$-dT$_3$dA$_{30}$ | DNA | 2573 | 1.3 |
| L(k)$_6$-dT$_3$-L(k)$_6$-dT$_3$dA$_{30}$ | LNA | 81970 | 43 |
| L(k)$_4$-d(k)$_2$-dT$_3$-L(k)$_4$-d(k)$_2$-dT$_3$dA$_{30}$ | LNA + DNA | 145128 | 76 |
| None (negative control) | — | 1379 | 0.7 |

In a second set of tests performed using the same target nucleic acid and target capture conditions as for the first set of tests in this example, different nonspecific capture probes all containing 18-nt nonspecific regions synthesized with 2'-methoxy linkages, and all with 3' DNA tails, were compared. Capture probes of (k)$_{18}$-dT$_3$dA$_{30}$ (SEQ ID NO:11), synthesized in the k18 portions by using a mixture of G:U bases of 50:50, 70:30, and 30:70 proportions, were compared to a capture probe of U$_{18}$-dT$_3$dA30 (SEQ ID NO:17) The results of these tests showed the relative efficiencies of these capture probes for capturing the target rRNA. The poly-U containing capture probe was least efficient (3.5% capture), the poly-k containing capture probe made by using G:U=70:30 was efficient (41% capture), and the poly-k containing capture probes made by using G:U=50:50 and 30:70 were more efficient (73% and 65% capture, respectively). Thus, comparative testing may be used to optimize probe design for nonspecific target capture.

Example 6: Target Capture Using Different Amounts of Nonspecific Capture Probes

This example shows that target capture reactions may be optimized by determining optimal amounts of nonspecific capture probes included in a reaction. These tests were performed using reaction mixtures and conditions substantially as described in Example 2, but using different amounts (e.g., 1-60 pmoles) of nonspecific capture probe per reaction. The target capture reactions were incubated at RT for 10-25 min before pellet portion was separated and the efficiency of capture was measured by detecting RLU in the pellet portion.

In the first set of tests, nonspecific capture probes containing 18-nt nonspecific regions were synthesized in different conformations and compared. The first conformation was (k)$_{18}$-dT$_3$dA$_{30}$ synthesized in the 5' portion with RNA bases and 2'-methoxy linkages, and in the 3' tail as DNA (SEQ ID NO:11) and the second was L(k)$_4$-d(k)$_3$-L(k)$_4$-d(k)$_3$-L(k)$_4$-dT$_3$dA$_{30}$ synthesized in the 5' portion with DNA bases in LNA and DNA conformation and in the 3' tail as DNA (SEQ ID NO:18). These two capture probes were tested separately using the same rRNA target but using 1, 2, 5, 10, 15, 20, 30 and 60 pmoles of capture probe per reaction, incubated at RT for 10 min. The results of these tests, shown in Table 10, show that capture was most efficient when about 15-30 pmoles of capture probe per reaction was used, and the capture probe with 2'-methoxy linkages in the backbone was somewhat more efficient than conformation with DNA and LNA residues.

TABLE 10

| Probe (pmoles) | $(k)_{18}$-dT$_3$dA$_{30}$ | | L(k)$_4$-d(k)$_3$-L(k)$_4$-d(k)$_3$-L(k)$_4$-dT$_3$dA$_{30}$ | |
|---|---|---|---|---|
| | RLU | % Capture | RLU | % Capture |
| 0 | 2023 | 1.2 | 2023 | 1.2 |
| 1 | 44634 | 26.8 | 35744 | 21.5 |
| 2 | 82760 | 49.7 | 53028 | 31.9 |
| 5 | 120224 | 72.3 | 67052 | 40.3 |
| 10 | 134893 | 81.1 | 91259 | 54.9 |
| 15 | 150664 | 90.6 | 112547 | 67.8 |
| 20 | 156844 | 94.3 | 121163 | 72.8 |
| 30 | 142370 | 85.6 | 113516 | 68.2 |
| 60 | 117035 | 70.4 | 108779 | 65.4 |

In a second set of tests, the nonspecific capture probes in the conformation $(k)_{18}$-dT$_3$dA$_{30}$ synthesized in the 5' portion with RNA bases and 2'-methoxy linkages (SEQ ID NO:11), was compared to a conformation that include in the 5' portion DNA and LNA but in the conformation L(k)$_3$-d(k)$_3$-L(k)$_3$-d(k)$_3$-L(k)$_3$-d(k)$_3$-dT$_3$dA$_{30}$ (SEQ ID NO:19). Both probes contained a 3' DNA tail. The reactions were performed substantially as described for the first set of tests in this example, except that the capture probes were used at 1, 2, 5, 10, 15, 20, 40 and 60 pmoles per reaction and incubation was at RT for 15 min. The results of these tests are shown in Table 11, which show that both conformations efficiently capture the RNA target but the LNA containing capture probe performs somewhat more efficiently at the lowest part of the concentration range tested.

TABLE 11

| Probe (pmoles) | $(k)_{18}$-dT$_3$dA$_{30}$ | | L(k)$_3$-d(k)$_3$-L(k)$_3$-d(k)$_3$-L(k)$_3$-d(k)$_3$-dT$_3$dA$_{30}$ | |
|---|---|---|---|---|
| | RLU | % Capture | RLU | % Capture |
| 0 | 1306 | 0.9 | 1306 | 0.9 |
| 1 | 25311 | 18.4 | 33600 | 24.4 |
| 2 | 49183 | 35.7 | 55354 | 40.2 |
| 5 | 85464 | 62.1 | 102750 | 74.7 |
| 10 | 123252 | 89.6 | 136135 | 99 |
| 15 | 142610 | 100 | 154470 | 100 |
| 20 | 146888 | 100 | 144039 | 100 |
| 40 | 139422 | 100 | 123765 | 90 |
| 60 | 132235 | 96.1 | 139610 | 100 |

Another set of tests were similarly performed using two different conformations of $K_{18}$ capture probes containing DNA and LNA residues. One conformation was L(k)$_4$-d(k)$_3$-L(k)$_4$-d(k)$_3$-L(k)$_4$-dT$_3$dA$_{30}$ (SEQ ID NO:18) and the other was L(k)$_3$-d(k)$_3$-L(k)$_3$-d(k)$_3$-L(k)$_3$-d(k)$_3$-dT$_3$dA$_{30}$ (SEQ ID NO:19) and were tested as described above by using 0, 1, 2, 5, 10, 15, 20, 40 and 60 pmoles of capture probe per reaction, incubated at RT for 10 min. The two conformations performed target capture similarly in the 1-60 pmole range (15 to 50% capture for the SEQ ID NO:18 probe and 21 to 65% capture for the SEQ ID NO:19 probe), with capture most efficient in the range of 15-40 pmoles of probe per reaction (45 to 50% for the first probe and 58 to 65% for the second probe). The same probes were used in a separate test using the same target rRNA and range of amounts of captures probes, but incubated at RT for 25 min. In these tests, over the 1-60 pmole range, the SEQ ID NO:18 probe captured 16 to 87% of the target and the SEQ ID NO:19 probe captured 27 to 100% of the target, with the most efficient capture for both probes in the 10-60 pmole range.

A similar set of tests were performed using two different conformations of nonspecific $k_{18}$ capture probes (SEQ ID NO:11), both synthesized nonspecific 5' regions having 2'-methoxy linkages and a 3' DNA tail. One conformation was synthesized with RNA bases (equimolar G and U, SEQ ID NO:20), and one was synthesized with DNA bases (equimolar G and T, SEQ ID NO:14). The two different conformations were tested as described above by using 0, 1, 2, 5, 10, 15, 20, 30 and 60 pmoles of capture probe per reaction, incubated at RT for 10 min. The two capture probes performed target capture similarly in the 1-60 pmole range (15 to 85% capture for the G/U probe and 21 to 90% capture for the G/T probe), with capture most efficient in the range of 15-30 pmoles of probe per reaction (78 to 85% for the G/U probe and 86 to 90% capture for the G/T probe).

Similar tests were performed to compare a nonspecific probes of $(GU)_9$-dT$_3$dA$_{30}$ (SEQ ID NO:21) and $(G/U)_{18}$-dT$_3$dA$_{30}$ (SEQ ID NO:20), both synthesized with 5' regions having RNA bases and 2'-methoxy linkages. The two capture probes were tested separately with the same target rRNA by using 0, 1, 2, 5, 10, 15, 20, 40 and 60 pmoles of capture probe per reaction, incubated at RT for 25 min. The two capture probes performed target capture similarly in the 1-60 pmole range (17 to 96% capture for SEQ ID NO:20 probe and 7 to 91% capture for the SEQ ID NO:21 probe), with capture most efficient in the range of 10-40 pmoles of probe per reaction (87 to 96% for the SEQ ID NO:20 probe and 75 to 91% capture for the SEQ ID NO:21 probe).

Example 7: Target Capture of DNA Targets Using Nonspecific Capture Probes

This example shows that nonspecific target capture probes effectively capture target DNA from a sample. The target DNA was either ssDNA, using a synthetic single strand consisting of SEQ ID NO:22: CCTCCATTCCGTTAC-CAACAGAACTGGAGGCGGTACAATGGGTCTTG TCATCCGGTAAAGGCCAAATATACGAGCATCAA-CATATGTACTTATGTATGTATCTA CTATATACATA-CATATGTACATATATGAATACCATCAGTCTGTGCAGT, or a substantially dsDNA made by hybridizing the ssDNA strand of SEQ ID NO:22 with a complementary strand (SEQ ID NO:23) which leaves a portion of the ssDNA strand available to hybridize to a complementary detection probe. The ssDNA or dsDNA was labeled by hybridizing it to a labeled probe (200 fmol of target DNA hybridized in a 0.04 ml solution with 1 pmole of AE-labeled probe at 60° C. for 1 hr, then diluted with 0.4 ml of an aqueous buffered solution). Target capture reactions contained an aliquot (0.01 ml) of the probe-labeled target DNA mixed with 0.5 ml containing 0.2 ml sample transport buffer, 0.2 ml water, and 0.1 ml TCR containing immobilized poly-dT on magnetic particles and 20 pmoles of the capture probe to be tested. The target capture reactions were incubated at RT for 1 hr, and then treated to pellet the captured complex, wash the captured complex once (0.5 ml wash solution) and detect the RLU, substantially as described in Example 1.

In a first set of tests, the nonspecific capture probes used were all or two of the following:

$(k)_{18}$-dT$_3$dA$_{30}$ (SEQ ID NO:11), with the 5' portion synthesized with RNA bases and 2'-methoxy linkages, d(k)$_6$-dT$_3$-d(k)$_6$-dT$_3$dA$_{30}$ (SEQ ID NO:10), with the 5' portion synthesized as DNA only;

L(k)$_6$-dT$_3$-L(k)$_6$-dT$_3$dA$_{30}$ (SEQ ID NO:24), with the 5' portion synthesized as LNA and DNA; and L(k)$_4$-d(k)$_2$-dT$_3$-L(k)$_4$-d(k)$_2$-dT$_3$dA$_{30}$ (SEQ ID NO:25), with the 5' portion synthesized as LNA and DNA.

Negative controls were samples treated identically but the target capture reaction mixtures did not contain any capture probe. The results of these tests are shown in Table 12. These results illustrate that a ssDNA target can be captured by using nonspecific capture probes and the probe's structure affects the efficiency of capture.

TABLE 12

| Capture Probe | ssDNA | | dsDNA | |
|---|---|---|---|---|
| | RLU | % Capture | RLU | % Capture |
| (k)$_{18}$-dT$_3$dA$_{30}$ | 8968 | 23 | 1893 | 5.4 |
| d(k)$_6$-dT$_3$-d(k)$_6$-dT$_3$dA$_{30}$ | 190 | 0.5 | — | — |
| L(k)$_6$-dT$_3$-L(k)$_6$-dT$_3$dA$_{30}$ | 4023 | 10 | — | — |
| L(k)$_4$-d(k)$_2$-dT$_3$-L(k)$_4$-d(k)$_2$-dT$_3$dA$_{30}$ | 18654 | 50 | 1542 | 4.4 |
| None (negative control) | 157 | 0.4 | 1104 | 3.1 |

In another set of tests, target capture of ssDNA was performed as described above using different amounts (1-40 pmoles) of the k$_{18}$ capture probes in different conformations. One conformation was (k)$_{18}$-dT$_3$dA$_{30}$ with the 5' nonspecific portion synthesized with 2'-methoxy RNA groups and a 3' DNA tail (SEQ ID NO:11), and another conformation was L(k)$_4$-d(k)$_3$-L(k)$_4$-d(k)$_3$-L(k)$_4$-dT$_3$dA$_{30}$ with the 5' nonspecific portion made of LNA and DNA residues and a 3' DNA tail (SEQ ID NO:18). Negative controls were treated the same but contained no capture probe. The target capture reactions were incubated at RT for 10 min and the remaining assay steps were as described above. The results of these tests, shown in Table 13, demonstrate that the LNA/DNA capture probe was more efficient at nonspecific capture of ssDNA than the k$_{18}$ capture probe that had RNA residues and 2'-methoxy linkages in the backbone of the oligomer. For both capture probes, capture was efficient in the range of 15-40 pmoles of capture probe per reaction.

TABLE 13

| Capture Probe | (k)$_{18}$-dT$_3$dA$_{30}$ | | L(k)$_4$-d(k)$_3$-L(k)$_4$-d(k)$_3$-L(k)$_4$-dT$_3$dA$_{30}$ | |
|---|---|---|---|---|
| (pmoles/reaction) | RLU | % Capture | RLU | % Capture |
| 0 | 206 | 0.4 | 206 | 0.4 |
| 1 | 582 | 1.2 | 1715 | 3.5 |
| 2 | 1130 | 2.3 | 3393 | 6.9 |
| 5 | 3898 | 7.9 | 11839 | 23.7 |
| 10 | 7583 | 15.4 | 19283 | 39.2 |
| 15 | 10409 | 21.2 | 25487 | 51.9 |
| 20 | 12631 | 25.7 | 29779 | 60.6 |
| 30 | 12393 | 25.2 | 31512 | 64.1 |
| 40 | 11240 | 22.8 | 30427 | 61.9 |

In the next set of tests, two km capture probes of in different LNA/DNA conformations were tested using different amounts (1-60 pmoles) of capture probe per reaction. The two conformations tested were: L(k)$_4$-d(k)$_3$-L(k)$_4$-d(k)$_3$-L(k)$_4$-dT$_3$dA$_{30}$ (SEQ ID NO:18) and L(k)$_3$-d(k)$_3$-L(k)$_3$-d(k)$_3$-L(k)$_3$-d(k)$_3$-dT$_3$dA$_{30}$ (SEQ ID NO:19). The target was ssDNA, captured in target capture reaction mixtures incubated at RT for 20 min, by using the method substantially as described above. The results of these tests are shown in Table 14, which show that the efficiency of capture is affected by the LNA/DNA capture probe's structure.

TABLE 14

| Capture Probe (pmoles) | L(k)$_4$-d(k)$_3$-L(k)$_4$-d(k)$_3$-L(k)$_4$-dT$_3$dA$_{30}$ (SEQ ID NO: 18) | | L(k)$_3$-d(k)$_3$-L(k)$_3$-d(k)$_3$-L(k)$_3$-d(k)$_3$-dT$_3$dA$_{30}$ (SEQ ID NO: 19) | |
|---|---|---|---|---|
| | RLU | % Capture | RLU | % Capture |
| 0 | 334 | 0.6 | 334 | 0.6 |
| 1 | 2007 | 3.5 | 2399 | 4.2 |
| 2 | 4740 | 8.2 | 5039 | 8.7 |
| 5 | 10936 | 18.9 | 16266 | 28.2 |
| 10 | 19969 | 34.6 | 29691 | 51.6 |
| 15 | 26958 | 46.8 | 37717 | 65.5 |
| 20 | 31295 | 54.3 | 43203 | 75 |
| 40 | 37419 | 64.9 | 39737 | 69 |
| 60 | 28135 | 48.8 | 38389 | 66.6 |

Using the same conditions as for the tests described immediately above, different LNA/DNA conformations of km nonspecific capture probes were tested for ssDNA target capture using 1-60 pmoles of capture probe per reaction. Capture probe of conformation L(k)$_4$-d(k)$_3$-L(k)$_4$-d(k)$_3$-L(k)$_4$-dT$_3$dA$_{30}$ (SEQ ID NO:18) captured ssDNA from 4 to 66% over the 1-60 pmole range, with efficient capture (54-66%) seen in the range of 15-60 pmoles. Capture probe of conformation L(k)$_2$-d(k)$_4$-L(k)$_2$-d(k)$_4$-L(k)$_2$-d(k)$_4$-dT$_3$dA$_{30}$ (SEQ ID NO:26) captured ssDNA from 2 to 62% over the 1-60 pmole range, with efficient capture (49-62%) seen in the range of 15-60 pmoles. The most efficient capture for both probes was seen when 40 pmoles were included in the reaction.

In another set of tests, the ssDNA target was captured by using nonspecific capture probes having (k)$_{12}$, (k)$_{18}$ or (k)$_{25}$ nonspecific sequences in different conformations, each probe tested individually using 20 pmoles per reaction as described above but incubated at RT for 30 min. The following (k)$_{12}$ capture probes were tested:

d(k)$_6$-dT$_3$-L(k)$_6$-dT$_3$dA$_{30}$ (SEQ ID NO:27),
L(k)$_6$-dT$_3$-L(k)$_6$-dT$_3$dA$_3$o (SEQ ID NO:15), and
L(k)$_4$-d(k)$_2$-dT$_3$-L(k)$_4$-d(k)$_2$-dT$_3$dA$_{30}$ (SEQ ID NO:25).

The three (k)$_{12}$ probes were compared to the following (k)$_{18}$ and (k)$_{25}$ capture probes:

L(k)$_4$-d(k)$_3$-L(k)$_4$-d(k)$_3$-L(k)$_4$-dT$_3$dA$_{30}$ (SEQ ID NO:18), and L(k)$_4$-d(k)$_3$-L(k)$_4$-d(k)$_3$-L(k)$_4$-d(k)$_3$-L(k)$_4$-dT$_3$dA$_{30}$ (SEQ ID NO:28, the (k)$_{25}$ probe).

Of these five capture probes, the (k)$_{18}$ and (k)$_{25}$ capture probes were most effective at ssDNA capture (74% and 77% respectively). Of the three (k)$_{12}$ capture probes tested, the first one that included no LNA (SEQ ID NO:27) was the least effective at ssDNA target capture (0.5%), whereas the two that included LNA conformation were more effective at ssDNA capture (15% for the SEQ ID NO:15 probe and 42% for the SEQ ID NO:25 probe). Based on the results of these and other tests for ssDNA capture performed using the same method, the relative efficiencies of $k_{18}$ nonspecific capture probes of different LNA/DNA conformations were determined as shown in the following list, with the most effective capture probe listed first: (1) $L(k)_3$-$d(k)_3$-$L(k)_3$-$d(k)_3$-$L(k)_3$-$d(k)_3$-$dT_3dA_{30}$, (2) $L(k)_4$-$d(k)_3$-$L(k)_4$-$d(k)_3$-$L(k)_4$-$dT_3dA_{30}$, (3) $L(k)_2$-$d(k)_4$-$L(k)_2$-$d(k)_4$-$L(k)_2$-$d(k)_4$-$dT_3dA_{30}$, (4) $L(k)_5$-$d(k)_2$-$L(k)_5$-$d(k)_2$-$L(k)_4$-$dT_3dA_{30}$, and (5) $L(k)_1$-$d(k)_5$-$L(k)_1$-$d(k)_5$-$L(k)_1$-$d(k)_5$-$dT_3dA_{30}$. Generally, nonspecific capture probes that contained a mixture of LNA and DNA conformations were more efficient for ssDNA target capture than capture probes of similar length that were in DNA conformation or synthesized using RNA bases with 2'-methoxy linkages in the nonspecific portion.

Example 8: Nonspecific Target Capture Using Non-Nucleic Acid Specific Binding Partners This example demonstrates nonspecific target capture by using a nonspecific capture probe that includes a first specific binding partner (SBP) that is not nucleic acid and that binds specifically to a second specific binding partner (SBP') that is the immobilized probe attached to a support. This was demonstrated by using a model system in which the SBP was biotin attached to an oligonucleotide containing the nonspecific binding region for the target nucleic acid, and the SBP' was streptavidin attached to magnetic particles (streptavidin-coupled DYNABEADS®, Invitrogen Corp., Carlsbad, CA). The model system uses the rRNA target prepared as described in Examples 1 and 2. The nonspecific capture probe was $(k)_{18}$-$dT_6$-Biotin (SEQ ID NO:29), synthesized in the 5' portion using RNA bases and 2'-methoxy linkages with biotin attached at the 3' terminus. The target capture reactions contained an aliquot (0.01 ml) of the probe-labeled rRNA (described in Example 1) mixed with 0.5 ml containing 0.2 ml sample transport buffer, 0.2 ml water, and 0.1 ml TCR and containing the biotin-derivatized capture probe bound specifically to the streptavidin-coupled magnetic beads via the specific binding pair of biotin and streptavidin. The target capture reactions were incubated at RT for 20 min, and then treated to pellet the captured complex as described in Example 1, the pellet portion was washed once with 0.5 ml wash solution, and the pellet portion was separated as before. Then the chemiluminescent signal from the AE-labeled probe attached to the target rRNA was detected as described in Example 1. Signal in the supernatant portion was also detected, which was 246310 RLU. The results of this experiment are shown in Table 15, showing that target capture mediated by a nonspecific capture probe attached via a specific binding pair to a support captures the RNA target, with the most efficient capture seen with about 60-120 m of streptavidin-derivatized particles were used.

TABLE 15

| Streptavidin-derivatized beads (μg) | RLU | % Capture |
| --- | --- | --- |
| 1 | 6890 | 2.8 |
| 2 | 11334 | 4.6 |
| 5 | 24107 | 9.8 |
| 10 | 50002 | 20.3 |
| 20 | 66559 | 27 |
| 40 | 104075 | 42 |
| 60 | 125467 | 51 |
| 120 | 133461 | 54 |

In a second test, using the same materials as described above, the kinetics of capture were detected by incubating the target capture mixtures for 2 to 60 min at RT before performing the separation of the complexes on the support from the solution phase and then performing the remaining steps as described above. All of these reactions were performed using 100 μg of the streptavidin-coupled magnetic beads with attached biotin derivatized capture probe. The time course of target capture is shown by the results presented in Table 16, which shows efficient capture in as little as 6 min with maximal capture in 60 min.

TABLE 16

| Incubation Time (min) | RLU | % Capture |
| --- | --- | --- |
| 2 | 43041 | 21 |
| 6 | 80229 | 39 |
| 15 | 120857 | 59 |
| 28 | 132916 | 65 |
| 60 | 190345 | 93 |

The invention claimed is:

1. A reaction mixture for isolating a target nucleic acid from a sample, said reaction mixture comprising:
   (a) a sample derived from cells that have been treated to release intracellular components, including the target nucleic acid, into a solution phase;
   (b) 15-40 pmol of a non-specific capture probe, wherein the non-specific capture probe comprises a first specific binding partner (SBP) and an oligonucleotide sequence wherein the oligonucleotide sequence is selected from the group consisting of:
   (i) two random poly-(k) sequences synthesized by random incorporation of G and T/U nucleotides separated by a spacer, wherein the total length of the two random poly-(k) sequences is at least 12 residues and wherein the spacer is selected from the group consisting of:
      (a) a non-random sequence represented by a formula $N_{1-10}$, wherein N is A/U/T/G/C;
      (b) a non-random sequence consisting of 10 or fewer inosine;
      (c) a non-random sequence consisting of 10 or fewer 5-nitroindole; and
      (d) a non-nucleotide spacer consisting of one or two C9 spacers;
   (ii) a plurality of random poly-(k) sequences synthesized by random incorporation of G and T/U nucleotides wherein the total length of the plurality of random poly-(k) sequences is at least 12 residues and wherein the random poly-(k) sequences are each separated by a spacer selected from the group consisting of:
      (a) non-random sequence represented by a formula $N_{1-10}$, wherein N is A/U/T/G/C;
      (b) a non-random sequence consisting of 10 or fewer inosine;
      (c) a non-random sequence consisting of 10 or fewer 5-nitroindole; or
      (d) a non-nucleotide spacer consisting of one or two C9 spacers;
   (iii) a non-random poly-GU sequence made up of at least six GU units; and
   (iv) a random poly-(k) sequence synthesized by random incorporation of G and T/U nucleotides wherein the random poly-(k) is at least 12 residues in length;

wherein the SBP comprises a homopolymeric nucleic acid sequence at least 14 nucleotides in length, a $dT_{0-3}dA_{30}$, or a non-nucleic acid moiety; and (c) a second specific binding partner (SBP'), wherein the SBP' is immobilized to a support, and wherein the SBP specifically binds the SBP'.

2. The reaction mixture of claim 1, wherein the solution phase comprises a detergent, lithium lauryl sulfate, or lithium hydroxide.

3. The reaction mixture of claim 1, wherein the sample comprises peripheral blood.

4. The reaction mixture of claim 1, wherein the oligonucleotide sequence contains one or more standard RNA bases and linkages, standard DNA bases and linkages, RNA bases with 2' modified linkages, or a combination thereof.

5. The reaction mixture of claim 4, wherein the oligonucleotide sequence comprises one or more 2'-O-methyl substituted RNA bases.

6. The reaction mixture of claim 1, wherein the SBP and SBP' are (a) non-nucleic acid moieties, or (b) substantially complementary nucleic acid sequences.

7. The reaction mixture of claim 6, wherein the non-nucleic acid moieties are selected from the group consisting of: (a) a receptor and ligand pair, (b) an enzyme and substrate pair, (c) an enzyme and cofactor pair, (d) an enzyme and coenzyme pair, (e) an antibody and antigen pair, (f) an antibody fragment and antigen pair, (g) a sugar and lectin pair, (h) a ligand and chelating agent pair, (i) biotin and avidin, (j) biotin and streptavidin, and (k) nickel and histidine.

8. The reaction mixture of claim 1, wherein the SBP (a) is situated 3' to the oligonucleotide sequence, or (b) is a $dT_3dA_{30}$ or $dA_{30}$ sequence, or (c) is (a) and (b).

9. The reaction mixture of claim 1, wherein the oligonucleotide sequence is selected from the group consisting of:
(k)6-Ni5-(k)6 in which "Ni" stands for 5-nitroindole,
(k)6-C9-C9-(k)6 in which "C9" stands for a C9 spacer,
(k)6-C9-(k)6-C9-(k)6 in which "C9" stands for a C9 spacer,
L(k)4-d(k)3-L(k)4-d(k)3-L(k)4,
L(k)3-d(k)3-L(k)3-d(k)3-L(k)3-d(k)3,
L(k)2-d(k)4-L(k)2-d(k)4-L(k)2-d(k)4, and
L(k)4-d(k)3-L(k)4-d(k)3-L(k)4-d(k)3-L(k) 4,
wherein d designates that the sequence has standard DNA conformation and L designates that the sequence is in a locked nucleic acid (LNA) conformation.

10. The reaction mixture of claim 1, wherein the oligonucleotide sequence is made up of two or more random poly-(k) sequences synthesized by random incorporation of G and T/U nucleotides separated by 1 to 2 C9 linkers or 1-5 5-nitroindole, and the SBP is $dT_3dA_{30}$, wherein each random poly-(k) sequence is 6-24 nucleotides in length.

11. The reaction mixture of claim 1, wherein the SBP' is linked to a magnetically attractable particle or a monodisperse paramagnetic bead.

12. A reaction mixture for isolating a target nucleic acid from a sample, the reaction mixture comprising:
a) a sample derived from cells that have been treated to release intracellular components, including the target nucleic acid, into a solution phase;
b) 15-40 pmol of a non-specific capture probe, wherein the non-specific capture probe comprises
(i) an oligonucleotide sequence that hybridizes nonspecifically to a target nucleic acid, wherein the oligonucleotide sequence comprises a randomized poly-(k) sequence synthesized by random incorporation of G and T nucleotides or G and U nucleotides, wherein the randomized poly-(k) sequence is 6 to 25 nucleotides in length and
(ii) a first specific binding partner (SBP) comprising a homopolymeric sequence; and
(c) a second specific binding partner (SBP') wherein the SBP' is immobilized to a support and contains a sequence that hybridizes specifically to the SBP.

13. The reaction mixture of claim 12, wherein the solution phase comprises a detergent, lithium lauryl sulfate, or lithium hydroxide.

14. The reaction mixture of claim 12, wherein the sample comprises peripheral blood.

15. The reaction mixture of claim 12, wherein the oligonucleotide sequence contains one or more standard RNA bases and linkages, standard DNA bases and linkages, RNA bases with 2' modified linkages, or a combination thereof.

16. The reaction mixture of claim 12, wherein the oligonucleotide sequence contains a mixture of nucleotides in LNA conformation and standard DNA conformation.

17. The reaction mixture of claim 12, wherein the randomized poly-(k) sequence is 12 to 25 nucleotides in length.

18. The reaction mixture of claim 12, wherein the SBP comprises
$dT_3dA_3LA_1dA_3LA_1dA_1LA_1dA_1LA_1dA_3LA_1dA_3LA_1dA_1LA_1dA_1LA_2dA_3LA_1dA_1$, wherein d designates that the sequence has a standard DNA conformation and L designates that the sequence is in a locked nucleic acid (LNA) conformation.

19. The reaction mixture of claim 12, wherein the oligonucleotide sequence is selected from the group consisting of:
$(k)_6$,
$(k)_{12}$,
$(k)_{18}$,
$(k)_{24}$,
$(k)_{25}$,
$L(k)_4-d(k)_3-L(k)_4-d(k)_3-L(k)_4$,
$L(k)_3-d(k)_3-L(k)_3-d(k)_3-L(k)_3-d(k)_3$,
$L(k)_2-d(k)_4-L(k)_2-d(k)_4-L(k)_2-d(k)_4$, and
$L(k)_4-d(k)_3-L(k)_4-d(k)_3-L(k)_4-d(k)_3-L(k)_4$,
wherein d designates that the sequence has standard DNA conformation and L designates that the sequence is in a locked nucleic acid (LNA) conformation.

20. The reaction mixture of claim 18, wherein the SBP' comprises $dT_{14}$.

* * * * *

UNITED STATES PATENT AND TRADEMARK OFFICE
CERTIFICATE OF CORRECTION

Page 1 of 2

PATENT NO. : 12,139,706 B2
APPLICATION NO. : 17/126693
DATED : November 12, 2024
INVENTOR(S) : Michael M. Becker et al.

It is certified that error appears in the above-identified patent and that said Letters Patent is hereby corrected as shown below:

On the Title Page

Item (56), under "OTHER PUBLICATIONS", in Column 2, Line 60, delete "the" and insert -- The --, therefor.

In the Specification

In Column 1, Line 7, delete "2016, allowed," and insert -- 2016, now U.S. Pat. No. 10,900,033, --, therefor.

In Column 1, Line 8, delete "13/769,226, is" and insert -- 13/769,226, filed Feb. 15, 2013, now abandoned, which is --, therefor.

In Column 1, Line 10, delete "2007," and insert -- 2007, now U.S. Pat. No. 9,051,601, --, therefor.

In Column 1, Line 12, delete "Aug. 17, 2006," and insert -- August 1, 2006, --, therefor.

In Column 3, Line 39, delete "poly-(k)$_2$5" and insert -- poly-(k)$_{25}$ --, therefor.

In Column 3, Line 49, delete "a (k)$_2$4 sequence, d(G or Mg" and insert -- a (k)$_{24}$ sequence, d(G or T)$_{18}$ --, therefor.

In Column 3, Line 52, delete "sequence)," and insert -- sequence, --, therefor.

In Column 3, Line 55, delete "L(k)6-dT3-L(k)6" and insert -- L(k)$_6$-dT$_3$-L(k)$_6$ --, therefor.

In Column 5, Line 6, delete ""SBP-poly-(k)"or" and insert -- "SBP-poly-(k)" or --, therefor.

In Column 8, Lines 54-55, delete "deoxygaunosine," and insert -- deoxyguanosine, --, therefor.

Signed and Sealed this
Fourth Day of February, 2025

Coke Morgan Stewart
*Acting Director of the United States Patent and Trademark Office*

CERTIFICATE OF CORRECTION (continued) Page 2 of 2
U.S. Pat. No. 12,139,706 B2

In Column 10, Line 33, delete "immobilize" and insert -- immobilized --, therefor.

In Column 16, Line 56, delete "(Seradyne)" and insert -- (Seradyn) --, therefor.

In Column 17, Line 21, delete "dT$_3$dA3o" and insert -- dT$_3$dA$_{30}$ --, therefor.

In Column 20, Line 6, delete "dT3dA3o," and insert -- dT$_3$dA$_{30}$, --, therefor.

In Column 23, Line 47, delete "show" and insert -- shown --, therefor.

In Column 24, Line 27, delete "show" and insert -- shown --, therefor.

In Column 24, Line 52, delete "show" and insert -- shown --, therefor.

In Column 25, Line 33, delete "dT3dA3o" and insert -- dT$_3$dA$_{30}$ --, therefor.

In Column 25, Line 41, delete "L(k)$_6$-dT$_3$-L(k)$_6$-dT$_3$dA$_3$o" and insert -- L(k)$_6$-dT$_3$-L(k)$_6$-dT$_3$dA$_{30}$ --, therefor.

In Column 26, Line 24, delete "k18" and insert -- k$_{18}$ --, therefor.

In Column 26, Line 26, delete "U$_{18}$-dT$_3$dA30" and insert -- U$_{18}$-dT$_3$dA$_{30}$ --, therefor.

In Column 28, Line 3, delete "captures" and insert -- capture --, therefor.

In Column 28, Line 45, delete "CTA    C" and insert -- CTAC --, therefor.

In Column 28, Line 67, delete "linkages," and insert -- linkages; --, therefor.

In Column 29, Line 58, in Table 13, delete "11839" and insert -- 11639 --, therefor.

In Column 30, Line 2, delete "d(k)$_3$-L(k)$_4$-dT$_3$dA$_3$o" and insert -- d(k)$_3$-L(k)$_4$-dT$_3$dA$_{30}$ --, therefor.

In Column 30, Line 51, delete "L(k)$_6$-dT$_3$-L(k)$_6$-dT$_3$dA$_3$o" and insert -- L(k)$_6$-dT$_3$-L(k)$_6$-dT$_3$dA$_{30}$ --, therefor.

In Column 32, Line 6, delete "m" and insert -- µg --, therefor.

In the Claims

In Column 58, Line 7, in Claim 12, delete "comprises" and insert -- comprises: --, therefor.

In Column 58, Line 13, in Claim 12, delete "length and" and insert -- length; and --, therefor.

In Column 58, Line 33, in Claim 18, delete "comprises" and insert -- comprises: --, therefor.

SEQUENCE LISTING

<160> NUMBER OF SEQ ID NOS: 52

<210> SEQ ID NO 1
<211> LENGTH: 48
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: misc_feature
<222> LOCATION: (10)..(15)
<223> OTHER INFORMATION: n is a, c, g, t or u

<400> SEQUENCE: 1
nnnnnnuuun nnnnntttaa aaaaaaaaaa aaaaaaaaaa aaaaaaaa        48

<210> SEQ ID NO 2

```
<211> LENGTH: 50
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: modified_base
<222> LOCATION: (7)..(11)
<223> OTHER INFORMATION: 5'-nitroindole

<400> SEQUENCE: 2
nnnnnnnnnn nnnnnnnttt aaaaaaaaaa aaaaaaaaaa aaaaaaaaaa                    50

<210> SEQ ID NO 3
<211> LENGTH: 50
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (7)..(11)
<223> OTHER INFORMATION: 5'-nitroindole
<220> FEATURE:
<221> NAME/KEY: misc_feature
<222> LOCATION: (7)..(11)
<223> OTHER INFORMATION: n is a, c, g, t or u

<400> SEQUENCE: 3 kkkkkknnnnn nkkkkkktttt aaaaaaaaaa aaaaaaaaaa aaaaaaaaaa                    50

<210> SEQ ID NO 4
<211> LENGTH: 45
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(12)
<223> OTHER INFORMATION: inosine
<220> FEATURE:
<221> NAME/KEY: misc_feature
<222> LOCATION: (1)..(12)
<223> OTHER INFORMATION: n is a, c, g, or t

<400> SEQUENCE: 4
nnnnnnnnnn nntttaaaaa aaaaaaaaaa aaaaaaaaaa aaaaa                           45

<210> SEQ ID NO 5
<211> LENGTH: 45
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (6)..(7)
<223> OTHER INFORMATION: two C-9 non-nucleotide spacers inserted between
      nt 6 and nt 7

<400> SEQUENCE: 5
kkkkkkkkkk kktttaaaaa aaaaaaaaaa aaaaaaaaaa aaaaa                           45

<210> SEQ ID NO 6
<211> LENGTH: 51
<212> TYPE: DNA
```

```
<213> ORGANISM: Artificial
<220> FEATURE:
<223> OTHER INFORMATION: synthetic oligonucleotide
<220> FEATURE:
<221> NAME/KEY: misc_structure
<222> LOCATION: (6)..(7)
<223> OTHER INFORMATION: one C-9 non-nucleotide spacer inserted between
      nt 6 and nt 7
<220> FEATURE:
<221> NAME/KEY: misc_structure
<222> LOCATION: (12)..(13)
<223> OTHER INFORMATION: one C-9 non-nucleotide spacer inserted between
      nt 12 and nt13

<400> SEQUENCE: 6
kkkkkkkkkk kkkkkkkktt taaaaaaaaa aaaaaaaaaa aaaaaaaaaa a            51

<210> SEQ ID NO 7
<211> LENGTH: 45
<212> TYPE: DNA
<213> ORGANISM: Artificial
<220> FEATURE:
<223> OTHER INFORMATION: synthetic oligonucleotide

<400> SEQUENCE: 7
kkkkkkkkkk kktttaaaaa aaaaaaaaaa aaaaaaaaaa aaaaa                   45

<210> SEQ ID NO 8
<211> LENGTH: 48
<212> TYPE: DNA
<213> ORGANISM: Artificial
<220> FEATURE:
<223> OTHER INFORMATION: synthetic oligonucleotide

<400> SEQUENCE: 8
kkkkkkuuuk kkkkktttaa aaaaaaaaaa aaaaaaaaaa aaaaaaaa                48

<210> SEQ ID NO 9
<211> LENGTH: 51
<212> TYPE: DNA
<213> ORGANISM: Artificial
<220> FEATURE:
<223> OTHER INFORMATION: synthetic oligonucleotide

<400> SEQUENCE: 9
kkkkkkuuuu uukkkkkktt taaaaaaaaa aaaaaaaaaa aaaaaaaaaa a            51

<210> SEQ ID NO 10
<211> LENGTH: 48
<212> TYPE: DNA
<213> ORGANISM: Artificial
<220> FEATURE:
<223> OTHER INFORMATION: synthetic oligonucleotide

<400> SEQUENCE: 10
kkkkkktttk kkkkktttaa aaaaaaaaaa aaaaaaaaaa aaaaaaaa                48

<210> SEQ ID NO 11
<211> LENGTH: 51
<212> TYPE: DNA
<213> ORGANISM: Artificial
<220> FEATURE:
<223> OTHER INFORMATION: synthetic oligonucleotide

<400> SEQUENCE: 11
kkkkkkkkkk kkkkkkkktt taaaaaaaaa aaaaaaaaaa aaaaaaaaaa a            51
```

```
<210> SEQ ID NO 12
<211> LENGTH: 57
<212> TYPE: DNA
<213> ORGANISM: Artificial
<220> FEATURE:
<223> OTHER INFORMATION: synthetic oligonucleotide

<400> SEQUENCE: 12
kkkkkkkkkk kkkkkkkkkk kkkktttaaa aaaaaaaaaa aaaaaaaaaa aaaaaaa      57

<210> SEQ ID NO 13
<211> LENGTH: 51
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (25)..(25)
<223> OTHER INFORMATION: locked nucleic acid (LNA)
<220> FEATURE:
<221> NAME/KEY: misc_structure
<222> LOCATION: (29)..(29)
<223> OTHER INFORMATION: locked nucleic acid (LNA)
<220> FEATURE:
<221> NAME/KEY: misc_structure
<222> LOCATION: (31)..(31)
<223> OTHER INFORMATION: locked nucleic acid (LNA)
<220> FEATURE:
<221> NAME/KEY: misc_structure
<222> LOCATION: (33)..(33)
<223> OTHER INFORMATION: locked nucleic acid (LNA)
<220> FEATURE:
<221> NAME/KEY: misc_structure
<222> LOCATION: (37)..(37)
<223> OTHER INFORMATION: locked nucleic acid (LNA)
<220> FEATURE:
<221> NAME/KEY: misc_structure
<222> LOCATION: (41)..(41)
<223> OTHER INFORMATION: locked nucleic acid (LNA)
<220> FEATURE:
<221> NAME/KEY: misc_structure
<222> LOCATION: (43)..(43)
<223> OTHER INFORMATION: locked nucleic acid (LNA)
<220> FEATURE:
<221> NAME/KEY: misc_structure
<222> LOCATION: (45)..(46)
<223> OTHER INFORMATION: locked nucleic acid (LNA)
<220> FEATURE:
<221> NAME/KEY: misc_structure
<222> LOCATION: (50)..(50)
<223> OTHER INFORMATION: locked nucleic acid (LNA)

<400> SEQUENCE: 13
kkkkkkkkkk kkkkkkkktt taaaaaaaaa aaaaaaaaa aaaaaaaaaa a      51

<210> SEQ ID NO 14
<211> LENGTH: 51
<212> TYPE: DNA
<213> ORGANISM: Artificial
<220> FEATURE:
<223> OTHER INFORMATION: synthetic oligonucleotide

<400> SEQUENCE: 14
kkkkkkkkkk kkkkkkkktt taaaaaaaaa aaaaaaaaa aaaaaaaaaa a      51

<210> SEQ ID NO 15
<211> LENGTH: 48
<212> TYPE: DNA
<213> ORGANISM: Artificial
<220> FEATURE:
<223> OTHER INFORMATION: synthetic oligonucleotide
<220> FEATURE:
```

<221> NAME/KEY: misc_structure
<222> LOCATION: (1)..(6)
<223> OTHER INFORMATION: locked nucleic acid (LNA)
<220> FEATURE:
<221> NAME/KEY: misc_structure
<222> LOCATION: (10)..(15)
<223> OTHER INFORMATION: locked nucleic acid (LNA)

<400> SEQUENCE: 15
kkkkkktttk kkkkktttaa aaaaaaaaaa aaaaaaaaaa aaaaaaaa                48

<210> SEQ ID NO 16
<211> LENGTH: 48
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (10)..(13)
<223> OTHER INFORMATION: locked nucleic acid (LNA)

<400> SEQUENCE: 16
kkkkkktttk kkkkktttaa aaaaaaaaaa aaaaaaaaaa aaaaaaaa                48

<210> SEQ ID NO 17
<211> LENGTH: 51
<212> TYPE: DNA
<213> ORGANISM: Artificial
<220> FEATURE:
<223> OTHER INFORMATION: synthetic oligonucleotide

<400> SEQUENCE: 17
uuuuuuuuuu uuuuuuuutt taaaaaaaaa aaaaaaaaaa aaaaaaaaaa a            51

<210> SEQ ID NO 18
<211> LENGTH: 51
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (8)..(11)
<223> OTHER INFORMATION: locked nucleic acid (LNA)
<220> FEATURE:
<221> NAME/KEY: misc_structure
<222> LOCATION: (15)..(18)
<223> OTHER INFORMATION: locked nucleic acid (LNA)

<400> SEQUENCE: 18
kkkkkkkkkk kkkkkkkktt taaaaaaaaa aaaaaaaaaa aaaaaaaaaa a            51

<210> SEQ ID NO 19
<211> LENGTH: 51
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(3)
<223> OTHER INFORMATION: locked nucleic acid (LNA)

```
<220> FEATURE:
<221> NAME/KEY: misc_structure
<222> LOCATION: (7)..(9)
<223> OTHER INFORMATION: locked nucleic acid (LNA)
<220> FEATURE:
<221> NAME/KEY: misc_structure
<222> LOCATION: (13)..(15)
<223> OTHER INFORMATION: locked nucleic acid (LNA)

<400> SEQUENCE: 19
kkkkkkkkkk kkkkkkkktt taaaaaaaaa aaaaaaaaaa aaaaaaaaaa a          51

<210> SEQ ID NO 20
<211> LENGTH: 51
<212> TYPE: DNA
<213> ORGANISM: Artificial
<220> FEATURE:
<223> OTHER INFORMATION: synthetic oligonucleotide
<220> FEATURE:
<221> NAME/KEY: RNA
<222> LOCATION: (1)..(18)
<223> OTHER INFORMATION: random G/U sequence

<400> SEQUENCE: 20
kkkkkkkkkk kkkkkkkktt taaaaaaaaa aaaaaaaaaa aaaaaaaaaa a          51

<210> SEQ ID NO 21
<211> LENGTH: 51
<212> TYPE: DNA
<213> ORGANISM: Artificial
<220> FEATURE:
<223> OTHER INFORMATION: synthetic oligonucleotide

<400> SEQUENCE: 21
gugugugugu gugugugutt taaaaaaaaa aaaaaaaaaa aaaaaaaaaa a          51

<210> SEQ ID NO 22
<211> LENGTH: 152
<212> TYPE: DNA
<213> ORGANISM: Artificial
<220> FEATURE:
<223> OTHER INFORMATION: synthetic oligonucleotide

<400> SEQUENCE: 22
cctccattcc gttaccaaca gaactggagg cggtacaatg ggtcttgtca tccggtaaag   60
gccaaatata cgagcatcaa catatgtact tatgtatgta tctactatat acatacatat  120
gtacatatat gaataccatc agtctgtgca gt                                152

<210> SEQ ID NO 23
<211> LENGTH: 121
<212> TYPE: DNA
<213> ORGANISM: Artificial
<220> FEATURE:
<223> OTHER INFORMATION: synthetic oligonucleotide

<400> SEQUENCE: 23
actgcacaga ctgatggtat tcatatatgt acatatgtat gtatatagta gatacataca   60
taagtacata tgttgatgct cgtatatttg gcctttaccg gatgacaaga cccattgtac  120
c                                                                  121

<210> SEQ ID NO 24
<211> LENGTH: 48
<212> TYPE: DNA
<213> ORGANISM: Artificial
<220> FEATURE:
```

```
<223> OTHER INFORMATION: synthetic oligonucleotide
<220> FEATURE:
<221> NAME/KEY: misc_structure
<222> LOCATION: (1)..(6)
<223> OTHER INFORMATION: locked nucleic acid (LNA)
<220> FEATURE:
<221> NAME/KEY: misc_structure
<222> LOCATION: (10)..(15)
<223> OTHER INFORMATION: locked nucleic acid (LNA)

<400> SEQUENCE: 24
kkkkkktttk kkkkktttaa aaaaaaaaaa aaaaaaaaaa aaaaaaaa                    48

<210> SEQ ID NO 25
<211> LENGTH: 48
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (10)..(13)
<223> OTHER INFORMATION: locked nucleic acid (LNA)

<400> SEQUENCE: 25
kkkkkktttk kkkkktttaa aaaaaaaaaa aaaaaaaaaa aaaaaaaa                    48

<210> SEQ ID NO 26
<211> LENGTH: 51
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(2)
<223> OTHER INFORMATION: locked nucleic acid (LNA)
<220> FEATURE:
<221> NAME/KEY: misc_structure
<222> LOCATION: (7)..(8)
<223> OTHER INFORMATION: locked nucleic acid (LNA)
<220> FEATURE:
<221> NAME/KEY: misc_structure
<222> LOCATION: (13)..(14)
<223> OTHER INFORMATION: locked nucleic acid (LNA)

<400> SEQUENCE: 26
kkkkkkkkkk kkkkkkkktt taaaaaaaaa aaaaaaaaaa aaaaaaaaaa a                 51

<210> SEQ ID NO 27
<211> LENGTH: 48
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (10)..(15)
<223> OTHER INFORMATION: locked nucleic acid (LNA)

<400> SEQUENCE: 27
kkkkkktttk kkkkktttaa aaaaaaaaaa aaaaaaaaaa aaaaaaaa                    48

<210> SEQ ID NO 28
<211> LENGTH: 58
<212> TYPE: DNA
<213> ORGANISM: Artificial
```

```
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (8)..(11)
<223> OTHER INFORMATION: locked nucleic acid (LNA)
<220> FEATURE:
<221> NAME/KEY: misc_structure
<222> LOCATION: (15)..(18)
<223> OTHER INFORMATION: locked nucleic acid (LNA)
<220> FEATURE:
<221> NAME/KEY: misc_structure
<222> LOCATION: (22)..(25)
<223> OTHER INFORMATION: locked nucleic acid (LNA)

<400> SEQUENCE: 28
kkkkkkkkkk kkkkkkkkkk kkkkktttaa aaaaaaaaaa aaaaaaaaaa aaaaaaaa         58

<210> SEQ ID NO 29
<211> LENGTH: 24
<212> TYPE: DNA
<213> ORGANISM: Artificial
<220> FEATURE:
<223> OTHER INFORMATION: synthetic oligonucleotide

<400> SEQUENCE: 29
kkkkkkkkkk kkkkkkkktt tttt                                             24

<210> SEQ ID NO 30
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: misc_feature
<222> LOCATION: (10)..(15)
<223> OTHER INFORMATION: n is a, c, g, t or u

<400> SEQUENCE: 30
nnnnnnuuun nnnnn                                                       15

<210> SEQ ID NO 31
<211> LENGTH: 17
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (1)..(17)
<223> OTHER INFORMATION: n is a, c, g, t or u
<220> FEATURE:
<221> NAME/KEY: modified_base
<222> LOCATION: (7)..(11)
<223> OTHER INFORMATION: 5'-nitroindole

<400> SEQUENCE: 31
nnnnnnnnnn nnnnnnn                                                     17

<210> SEQ ID NO 32
<211> LENGTH: 17
<212> TYPE: DNA
```

```
<213> ORGANISM: Artificial
<220> FEATURE:
<223> OTHER INFORMATION: synthetic oligonucleotide
<220> FEATURE:
<221> NAME/KEY: modified_base
<222> LOCATION: (7)..(11)
<223> OTHER INFORMATION: 5'-nitroindole
<220> FEATURE:
<221> NAME/KEY: misc_feature
<222> LOCATION: (7)..(11)
<223> OTHER INFORMATION: n is a, c, g, t or u

<400> SEQUENCE: 32
kkkkkknnnn nkkkkkk                                                  17

<210> SEQ ID NO 33
<211> LENGTH: 12
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(12)
<223> OTHER INFORMATION: inosine
<220> FEATURE:
<221> NAME/KEY: misc_feature
<222> LOCATION: (1)..(12)
<223> OTHER INFORMATION: n is a, c, g, t or u

<400> SEQUENCE: 33
nnnnnnnnnn nn                                                       12

<210> SEQ ID NO 34
<211> LENGTH: 12
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (6)..(7)
<223> OTHER INFORMATION: two C-9 non-nucleotide spacers inserted between
      nt 6 and nt 7

<400> SEQUENCE: 34
kkkkkkkkkk kk                                                       12

<210> SEQ ID NO 35
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (6)..(7)
<223> OTHER INFORMATION: one C-9 non-nucleotide spacer inserted between
      nt 6 and nt 7
<220> FEATURE:
<221> NAME/KEY: misc_structure
<222> LOCATION: (12)..(13)
<223> OTHER INFORMATION: one C-9 non-nucleotide spacer inserted between
      nt 12 and nt 13

<400> SEQUENCE: 35
kkkkkkkkkk kkkkkkkk                                                 18

<210> SEQ ID NO 36
<211> LENGTH: 12
<212> TYPE: DNA
```

```
<213> ORGANISM: Artificial
<220> FEATURE:
<223> OTHER INFORMATION: synthetic oligonucleotide

<400> SEQUENCE: 36
kkkkkkkkkk kk                                                      12

<210> SEQ ID NO 37
<211> LENGTH: 15
<212> TYPE: DNA
<213> ORGANISM: Artificial
<220> FEATURE:
<223> OTHER INFORMATION: synthetic oligonucleotide

<400> SEQUENCE: 37
kkkkkkuuuk kkkkk                                                   15

<210> SEQ ID NO 38
<211> LENGTH: 18
<212> TYPE: DNA
<213> ORGANISM: Artificial
<220> FEATURE:
<223> OTHER INFORMATION: synthetic oligonucleotide

<400> SEQUENCE: 38
kkkkkkuuuu uukkkkkk                                                18

<210> SEQ ID NO 39
<211> LENGTH: 15
<212> TYPE: DNA
<213> ORGANISM: Artificial
<220> FEATURE:
<223> OTHER INFORMATION: synthetic oligonucleotide

<400> SEQUENCE: 39
kkkkkktttk kkkkk                                                   15

<210> SEQ ID NO 40
<211> LENGTH: 18
<212> TYPE: DNA
<213> ORGANISM: Artificial
<220> FEATURE:
<223> OTHER INFORMATION: synthetic oligonucleotide

<400> SEQUENCE: 40
kkkkkkkkkk kkkkkkkk                                                18

<210> SEQ ID NO 41
<211> LENGTH: 24
<212> TYPE: DNA
<213> ORGANISM: Artificial
<220> FEATURE:
<223> OTHER INFORMATION: synthetic oligonucleotide

<400> SEQUENCE: 41
kkkkkkkkkk kkkkkkkkkk kkkk                                         24

<210> SEQ ID NO 42
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(6)
<223> OTHER INFORMATION: locked nucleic acid (LNA)
```

```
<220> FEATURE:
<221> NAME/KEY: misc_structure
<222> LOCATION: (10)..(15)
<223> OTHER INFORMATION: locked nucleic acid (LNA)

<400> SEQUENCE: 42
kkkkkktttk kkkkk                                                    15

<210> SEQ ID NO 43
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (10)..(13)
<223> OTHER INFORMATION: locked nucleic acid (LNA)

<400> SEQUENCE: 43
kkkkkktttk kkkkk                                                    15

<210> SEQ ID NO 44
<211> LENGTH: 18
<212> TYPE: RNA
<213> ORGANISM: Artificial
<220> FEATURE:
<223> OTHER INFORMATION: synthetic oligonucleotide

<400> SEQUENCE: 44
uuuuuuuuuu uuuuuuuu                                                 18

<210> SEQ ID NO 45
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (8)..(11)
<223> OTHER INFORMATION: locked nucleic acid (LNA)
<220> FEATURE:
<221> NAME/KEY: misc_structure
<222> LOCATION: (15)..(18)
<223> OTHER INFORMATION: locked nucleic acid (LNA)

<400> SEQUENCE: 45
kkkkkkkkkk kkkkkkkk                                                 18

<210> SEQ ID NO 46
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(3)
<223> OTHER INFORMATION: locked nucleic acid (LNA)
<220> FEATURE:
<221> NAME/KEY: misc_structure
<222> LOCATION: (7)..(9)
```

```
<223> OTHER INFORMATION: locked nucleic acid (LNA)
<220> FEATURE:
<221> NAME/KEY: misc_structure
<222> LOCATION: (13)..(15)
<223> OTHER INFORMATION: locked nucleic acid (LNA)

<400> SEQUENCE: 46
kkkkkkkkkk kkkkkkkk                                              18

<210> SEQ ID NO 47
<211> LENGTH: 18
<212> TYPE: RNA
<213> ORGANISM: Artificial
<220> FEATURE:
<223> OTHER INFORMATION: synthetic oligonucleotide

<400> SEQUENCE: 47
gugugugugu gugugugu                                              18

<210> SEQ ID NO 48
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(6)
<223> OTHER INFORMATION: locked nucleic acid (LNA)
<220> FEATURE:
<221> NAME/KEY: misc_structure
<222> LOCATION: (10)..(15)
<223> OTHER INFORMATION: locked nucleic acid (LNA)

<400> SEQUENCE: 48
kkkkkktttk kkkkk                                                 15

<210> SEQ ID NO 49
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (10)..(13)
<223> OTHER INFORMATION: locked nucleic acid (LNA)

<400> SEQUENCE: 49
kkkkkktttk kkkkk                                                 15

<210> SEQ ID NO 50
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(2)
<223> OTHER INFORMATION: locked nucleic acid (LNA)
<220> FEATURE:
<221> NAME/KEY: misc_structure
<222> LOCATION: (7)..(8)
<223> OTHER INFORMATION: locked nucleic acid (LNA)
<220> FEATURE:
<221> NAME/KEY: misc_structure
```

```
<222> LOCATION: (13)..(14)
<223> OTHER INFORMATION: locked nucleic acid (LNA)

<400> SEQUENCE: 50
kkkkkkkkkk kkkkkkkk                                                  18

<210> SEQ ID NO 51
<211> LENGTH: 15
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (10)..(15)
<223> OTHER INFORMATION: locked nucleic acid (LNA)

<400> SEQUENCE: 51
kkkkkktttk kkkkk                                                     15

<210> SEQ ID NO 52
<211> LENGTH: 25
<212> TYPE: DNA
<213> ORGANISM: Artificial
<220> FEATURE:
<223> OTHER INFORMATION: synthetic oligonucleotide
<220> FEATURE:
<221> NAME/KEY: misc_structure
<222> LOCATION: (1)..(4)
<223> OTHER INFORMATION: locked nucleic acid (LNA)
<220> FEATURE:
<221> NAME/KEY: misc_structure
<222> LOCATION: (8)..(11)
<223> OTHER INFORMATION: locked nucleic acid (LNA)
<220> FEATURE:
<221> NAME/KEY: misc_structure
<222> LOCATION: (15)..(18)
<223> OTHER INFORMATION: locked nucleic acid (LNA)
<220> FEATURE:
<221> NAME/KEY: misc_structure
<222> LOCATION: (22)..(25)
<223> OTHER INFORMATION: locked nucleic acid (LNA)

<400> SEQUENCE: 52
kkkkkkkkkk kkkkkkkkkk kkkkk                                          25
```